(12) United States Patent
Vandenbossche et al.

(10) Patent No.: US 10,435,351 B2
(45) Date of Patent: Oct. 8, 2019

(54) ENAMIDE PROCESS

(71) Applicant: SUNOVION PHARMACEUTICALS INC., Marlborough, MA (US)

(72) Inventors: Charles P. Vandenbossche, Waltham, MA (US); John R. Snoonian, Bolton, MA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

(21) Appl. No.: 15/882,498

(22) Filed: Jan. 29, 2018

(65) Prior Publication Data

US 2018/0215702 A1  Aug. 2, 2018

Related U.S. Application Data

(60) Provisional application No. 62/452,608, filed on Jan. 31, 2017.

(51) Int. Cl.
C07C 231/10 (2006.01)
C07C 249/08 (2006.01)
(Continued)

(52) U.S. Cl.
CPC .......... C07C 231/10 (2013.01); C07C 209/50 (2013.01); C07C 209/62 (2013.01);
(Continued)

(58) Field of Classification Search
None
See application file for complete search history.

(56) References Cited

U.S. PATENT DOCUMENTS

2009/0149549 A1* 6/2009 Zhao ................ C07B 43/06
514/657
2016/0016891 A1 1/2016 Zhao

FOREIGN PATENT DOCUMENTS

EP  2257518 B1  3/2016
WO  99/18065  4/1999
(Continued)

OTHER PUBLICATIONS

Saha ("Directing Group Assisted Nucleophilic Substitution of Propargylic Alcohols via o-Quinone Methide Intermediates: Bronsted Acid Catalyzed, Hlhgly Enantio- and Diastereoselective Synthesis of 7-Alkynyl-12a-acetamido-Substituted Benzoxanthenes" Org Lett, 2015, p. 648-651, including SI p. S1-S101). (Year: 2015).*
(Continued)

Primary Examiner — Amy C Bonaparte
(74) Attorney, Agent, or Firm — Heslin Rothenberg Farley & Mesiti, P.C.; Philip Hansen

(57) ABSTRACT

A convenient method for converting oximes into enamides is disclosed. The process produces enamides without the concomitant production of a large volume of metallic waste.

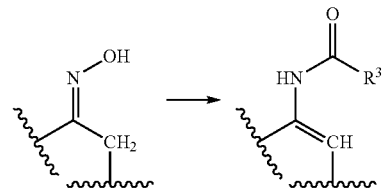

The enamides are useful precursors to amides and amines.

23 Claims, 3 Drawing Sheets

(51) Int. Cl.
*C07C 209/62* (2006.01)
*C07C 233/91* (2006.01)
*C07C 231/12* (2006.01)
*C07C 209/50* (2006.01)

(52) U.S. Cl.
CPC .......... *C07C 231/12* (2013.01); *C07C 233/91* (2013.01); *C07C 249/08* (2013.01); *C07B 2200/07* (2013.01); *C07C 2601/14* (2017.05); *C07C 2602/10* (2017.05)

(56) References Cited

FOREIGN PATENT DOCUMENTS

WO 2007056403 A2 5/2007
WO 2007/115185 A2 10/2007

OTHER PUBLICATIONS

International Search Report and WOISA from PCT/US18/15730 dated Mar. 5, 2018.
Tschaen, et al., Asymmetric Synthesis of MK-0499, American Chemical Society, J. Org. Chem., vol. 60, pp. 4324-4330, 1995.
Savarin, et al., Direct N-Acetyl Enamine Formation: Lithium Bromide Mediated Addition of Methyllithium to Nitriles, American Chemical Society, Organic Letters, vol. 8, No. 18, pp. 3903-3906, 2006.
Reeves, et al., Direct Titanium-Mediated Conversion of Ketones into Enamides with Ammonia and Acetic Anhydride, Angewandte Communications, Agnew Chem. Int. Ed., vol. 51, pp. 1400-1404, 2012.
Klapars, et al., Preparation of Enamides via Palladium-Catalyzed Amidation of Enol Tosylates, American Chemical Society, Organic Letters, vol. 7, No. 6, pp. 1185-1188, 2005.
Lindhardt Hansen, et al., Fast and Regioselective Heck Couplings with N-Acyl-N-vinylamine Derivatives, American Chemical Society, J. Org. Chem., JOC Article, vol. 70, pp. 5997-6003, 2005.
Burk, et al., A Three-Step Procedure for Asymmetric Catalytic Reductive Amidation of Ketones, American Chemical Society, J. Org. Chem., vol. 63, pp. 6084-6085, 1998.
Boar, et al., A Simple Synthesis of Enamides from Ketoximes, J.C.S. Perkin I, pp. 1237-1241. Dec. 5, 1974.
Barton, et al., A Further Synthesis of the Corticosteroid Side Chain starting with a Suitable 17-Ketone, J. Chem. Soc., Perkin Trans., pp. 2191-2192, 1985.
Savarin, et al., Novel Intramolecular Reactivity of Oximes: Synthesis of Cyclic and Spiro-Fused Imines, American Chemical Society, Organic Letters, vol. 9, No. 6, pp. 981-983, 2007.
Zhao, et al., An Efficient Synthesis of Enamides from Ketones, American Chemical Society, Organic Letters, vol. 10, No. 3, pp. 505-507, 2008.
Takai, et al., Generation of chromioenamines by reduction of O-acetyloximes with chromium (II) and their application, The Royal Society of Chemistry, Chem. Commun., pp. 1724-1725, 2001.
Tang, et al., A Facile and Practical Synthesis of N-Acetyl Enamides, American Chemical Society, J. Org. Chem., vol. 74, pp. 9258-9530, 2009.
Boivin, et al., A New Method for the Generation and Capture of Iminyl Radicals, Elsevier Science Ltd., Tetrahedron Letters, vol. 40 , pp. 4531-4534, 1999.
Guan, et al., Synthesis of Enamides via CuI-Catalyzed Reductive Acylation of Ketoximes with $NaHSO_3$, American Chemical Society, J. Org. Chem., JOC Note, vol. 76, pp. 339-341, 2011.
Deb, et al., Phenanthridine Synthesis through Iron-Catalyzed Intramolecular N-Arylation of O-Acetyl Oxime, American Chemical Society, Organic Letters, vol. 15, No. 16, pp. 4254-4257, 2013.
Guan, et al., Synthesis of Enamides via Rh/C-Catalyzed Direct Hydroacylation of Ketoximes, American Chemical Society, Organic Letters, vol. 11, No. 2, pp. 481-483, 2009.
Murugan, et al., An efficient preparation of N-acetyl enamides catalyzed by Ru(II) complexes, Elsevier Ltd., Tetrahedron, vol. 69, pp. 268-273, 2013.

* cited by examiner

ENAMIDE PROCESS

CROSS-REFERENCE TO RELATED APPLICATIONS

This application claims priority to U.S. provisional application 62/452,608, filed Jan. 31, 2017. The entire contents of U.S. 62/452,608 are incorporated herein by reference.

FIELD

Methods of preparing compounds using an iron catalyst, and related intermediates, are disclosed.

BACKGROUND

Enantiomerically-enriched chiral primary amines are commonly used as resolving agents for racemic acids, as chiral auxiliaries for asymmetric syntheses, and as ligands for transition metal catalysts used in asymmetric catalysis. In addition, many pharmaceuticals contain chiral amine moieties. Effective methods for the preparation of such compounds are of great interest to the pharmaceutical industry. Particularly valuable are processes that allow for the preparation of each enantiomer or diastereomer in enantiomeric excess (ee) or diastereomeric excess (de), as appropriate, from prochiral or chiral starting materials.

As a result of the large number of chiral catalysts which are now commercially available, chiral amines can be easily obtained from the catalytic asymmetric hydrogenation of N-acyl enamines (enamides). The preparation of an enantiomerically-enriched amine via conversion of a precursor oxime to the corresponding enamide, which is subsequently converted to the amine through asymmetric hydrogenation and deprotection, has been described in WO 99/18065. The oxime-to-enamide conversion process of WO 99/18065 is, however, not of general applicability to a wide range of substrates. Moreover, many of the recognized processes require a large excess of metallic reagent to effect the conversion. For example, Burk et al. [J. Org. Chem., 1998, 63, 6084] reported that enamides could be prepared in 30-80% yield by heating the oxime in toluene at 70° C. in the presence of 3.0 eq. of acetic anhydride and 2.0 eq. of iron powder. However, this method is unsuitable for large scale manufacture because (a) it generates large amounts of iron waste, and (b) the initiation of the rapidly exothermic reaction is unpredictable. A different process, employing a phosphine as reducing agent, is disclosed in WO 2007/115185. The process of WO 2007/115185 is a workable process, upon which the instant process is an improvement.

SUMMARY

The present disclosure provides an efficient and convenient method for the conversion of an oxime to the corresponding enamide. The method is appropriate for large-scale synthesis of enamides and, from the enamides, synthesis of amides, amines, and their derivatives.

In some embodiments, provided is a method for converting an oxime into an enamide. The method comprises contacting an oxime with an acyl donor and a phosphine in the presence of an iron reagent that provides from 10 to 2000 ppm iron. The reaction is carried out under conditions that convert the oxime to the enamide.

In some embodiments, provided is a method for converting a ketone to an enamide. The method comprises (a) first reacting a ketone with hydroxylamine to provide an oxime; and
(b) second reacting the oxime with an acyl donor and a phosphine in the presence of an iron reagent that provides from 10 to 2000 ppm iron.

In some embodiments, provided is a method for converting a prochiral ketone to an enantiomerically enriched chiral amide. The method comprises:

(a) first reacting a ketone with hydroxylamine to provide an oxime;
(b) second reacting the oxime with an acyl donor and a phosphine in the presence of an iron reagent that provides from 10 to 2000 ppm iron to provide an enamide; and
(c) third reducing the enamide with hydrogen in the presence of a chiral catalyst to produce an enantiomerically enriched chiral amide.

In some embodiments, provided is a method for converting a prochiral ketone to an enantiomerically enriched chiral amine. The method comprises:

(a) first reacting a ketone with hydroxylamine to provide an oxime;
(b) second reacting the oxime with an acyl donor and a phosphine in the presence of an iron reagent that provides from 10 to 2000 ppm iron to provide an enamide;
(c) third reducing the enamide with hydrogen in the presence of a chiral catalyst to produce an enantiomerically enriched chiral amide; and
(d) fourth hydrolyzing the chiral amide to an enantiomerically enriched chiral amine.

DETAILED DESCRIPTION

Figure 1:
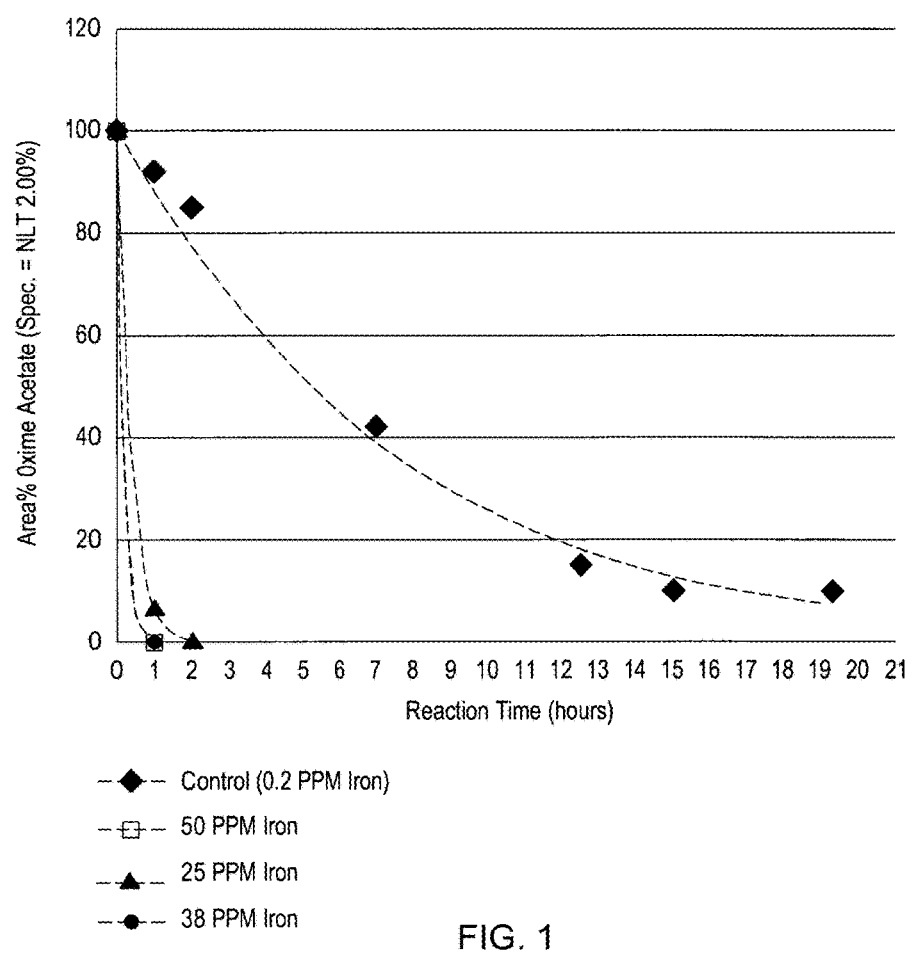
FIG. 1 is a graph of reaction speed reflected as percent residual oxime acetate versus time in hours in the presence of varying amounts of iron.

The description provided herein is made with the understanding that the present disclosure is to be considered as an exemplification of the claimed subject matter, and is not intended to limit the claims to the specific embodiments. The headings used throughout this disclosure are provided for convenience and are not to be construed to limit the claims in any way. Embodiments under any heading may be combined with embodiments under any other heading.

All published documents cited herein are hereby incorporated by reference in their entirety.

Definitions

The description provided herein uses certain terms in the chemical arts. Unless otherwise specified throughout the description herein, terms retain their meaning as understood by one having ordinary skill in the art.

As used herein, the terms "comprising" and "including" or grammatical variants thereof are to be taken as specifying the stated features, integers, steps or components, but do not preclude the addition of one or more additional features, integers, steps, components or groups thereof. This term encompasses the terms "consisting of" and "consisting essentially of". The phrase "consisting essentially of" or grammatical variants thereof, when used herein, are to be taken as specifying the stated features, integers, steps or components, but do not preclude the addition of one or more additional features, integers, steps, components or groups thereof, but only if the additional features, integers, steps, components or groups thereof do not materially alter the basic and novel characteristics of the claimed composition or method.

As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method that "comprises", "has", "includes" or "contains" one or more steps or elements possesses those one or more steps or elements, but is not limited to possessing only those one or more steps or elements.

Reference throughout the description to "one embodiment" or "an embodiment" or "some embodiments" means that a particular feature, structure or characteristic described in connection with the embodiment is included in at least that embodiment. Use of "one embodiment" or "an embodiment" or "some embodiments" throughout the description are not necessarily referring to the same embodiments; but particular features, structures, or characteristics may be combined in any suitable manner in one or more embodiments.

As used herein, methods comprising numbered steps (e.g., first, second, third, etc.) indicate that a first step occurs before a second step and a second step occurs before a third step, but does not necessarily preclude intermediate steps. For example, in "a method of converting a ketone (K) to an enamide (E):

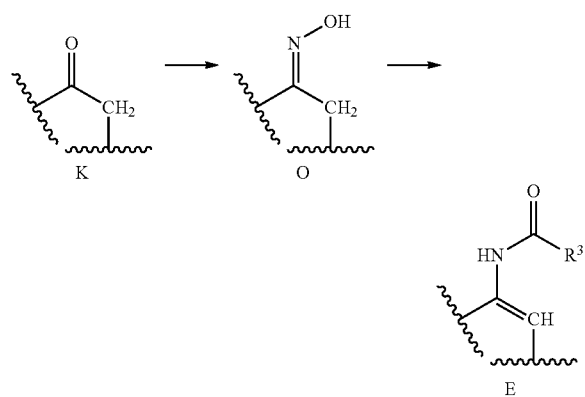

wherein the method comprises
  (a) first reacting a ketone with hydroxylamine to provide an oxime; and
  (b) second reacting the oxime with an acyl donor and a phosphorus reagent in the presence of an iron reagent as described herein,"
step (a) must occur before step (b) (e.g., step (a) precedes step (b)), but there may be one or more intermediate steps between (a) and (b), such as additional reactions or heating or washing or separating, etc. Accordingly, "first," "second," "third," etc. are sequential steps or events, but do not preclude intermediate steps between, for example, ("first" and "second") or ("second" and "third") steps.

A prefix such as "$C_x$-$C_y$" or "$(C_x$-$C_y)$" indicates that the group following said prefix has from x toy carbon atoms. For example, a "$C_1$ to $C_{20}$ hydrocarbon" indicates a hydrocarbon having 1 to 20 carbon atoms.

As used herein, "hydrocarbon" refers to radical comprising carbon atoms. In some embodiments, provided are $C_1$-$C_{20}$ hydrocarbons, which comprise 1 to 20 carbon atoms. Non-limiting examples of hydrocarbons include alkyl, cycloalkyl, polycycloalkyl, alkenyl, alkynyl, aryl and combinations thereof (e.g., arylalkyl). Non-limiting examples of $C_1$-$C_{20}$ hydrocarbons include methyl, ethyl, propyl, etc., cyclopropyl, phenyl, naphthyl, benzyl, phenethyl, cyclohexylmethyl, adamantyl, camphoryl and naphthylethyl.

As used herein, "hydrocarbyl" refers to any radical comprised of hydrogen and carbon as the only elemental constituents.

As used herein, "aliphatic hydrocarbons" are hydrocarbons that are not aromatic. An aliphatic hydrocarbon may be saturated or unsaturated and cyclic, linear or branched. Non-limiting examples of aliphatic hydrocarbons include isopropyl, 2-butenyl, 2-butynyl, cyclopentyl, norbornyl, etc.

As used herein, "aromatic hydrocarbons" include phenyl, naphthyl, anthracene, etc.

Unless otherwise specified, "alkyl" (or a related divalent radical "alkylene") is intended to include linear or branched saturated hydrocarbon structures and combinations thereof. In some embodiments, an alkyl may have 1 to 20 carbon atoms (e.g., $C_1$-$C_{20}$ alkyl), or 1 to 10 carbon atoms (e.g., $C_1$-$C_{10}$ alkyl), or 1 to 6 carbon atoms (e.g., $C_1$-$C_6$ alkyl). Non-limiting examples of alkyl groups include methyl, ethyl, propyl, isopropyl, n-butyl, s-butyl, t-butyl and the like.

As used herein, "Cycloalkyl" is a cyclic hydrocarbon. In some embodiments, a cycloalkyl may have 3 to 8 carbon atoms (e.g., $C_3$-$C_8$ cycloalkyl). Non-limiting examples of cycloalkyl groups include cy-propyl, cy-butyl, cy-pentyl, norbornyl and the like.

Unless otherwise specified, the term "carbocycle" is intended to include ring systems (monocyclic) in which the ring atoms are all carbon but of any oxidation state. Thus a carbocycle refers to both non-aromatic and aromatic systems. A "carbopolycycle" refers to a polycyclic (two or more rings) carbocycle. Non-limiting examples of $C_3$-$C_8$ carbocycles include cyclopropane, benzene and cyclohexene; and non-limiting examples of $C_8$-$C_{12}$ carbopolycycle include norbornane, decalin, indane and naphthalene.

As used herein, the term "acyl donor" refers to a compound capable of donating an acyl group under certain reaction conditions. In some embodiments, acyl donors are anhydrides of carboxylic acids, such as acetic anhydride. In some embodiments, the acyl donor is acetic anhydride. Reference throughout this description to an "acyl residue" refers to the hydrocarbon "$R^3$" group from an acyl donor. In some embodiments, the acyl residue (e.g., $R^3$) is a $C_1$-$C_6$ hydrocarbon. In some embodiments, the acyl residue (e.g., $R^3$) is methyl, pivaloyl or phenyl. In some embodiments, the acyl residue (e.g., $R^3$) is a $C_1$-$C_6$ alkyl. In some embodiments, the acyl residue (e.g., $R^3$) is methyl, ethyl, or propyl.

As used herein, the term "phosphine" refers to a phosphorus reagent having the following formula:

$$P(Q)_3$$

wherein each Q is independently selected from H, halogen, substituted or unsubstituted alkyl and substituted or unsubstituted aryl. In some embodiments, Q may be selected from $C_1$-$C_6$ alkyl and phenyl. In some embodiments, phosphorus reagents include, but are not limited to, diphenylphosphine ($Ph_2PH$), triphenylphosphine ($Ph_3P$), tri-n-butylphosphine (n-$Bu_3P$), triethylphosphine ($Et_3P$), tri-n-propylphosphine (n-$Pr_3P$), 1,2-bisdiphenylphosphinoethane ($Ph_2PCH_2CH_2PPh_2$), and chlorodiphenylphosphine ($Ph_2PCl$). In some embodiments, trialkyl phosphines (e.g., triethyl phosphine) are advantageous phosphorus reagents because a phosphine oxide by-product is easily removed from the reaction mixture at the end of the reaction. In some embodiments, the phosphorus reagent is triethylphosphine ($Et_3P$), In some embodiments, the phosphine is tri n-butylphosphine (n-$Bu_3P$), triethyl phosphine ($Et_3P$), diphenylphosphinoethane ($Ph_2PCH_2CH_2PPh_2$), or triphenyl phosphine ($Ph_3P$). In some embodiments, the phosphine is triethylphosphine ($Et_3P$), As used herein, the term "optionally substituted" may be used interchangeably with "unsubstituted or substituted". The term "substituted" refers to the replacement of one or more hydrogen atoms in a specified group with a specified radical. For example, "substituted hydrocarbyl" refers to a hydrocarbon in which one or more hydrogen atoms are replaced with halogen, haloalkyl, acyl, alkoxy, haloalkoxy, oxaalkyl, cyano, acetoxy, phenoxy, benzyloxy, and the like. As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein, the term "substantially optically pure" refers to a non-racemic mixture of isomers in which one isomer constitutes at least 80% of the mixture. In a preferred embodiment, the term "substantially optically pure" means that the compound is made up of at least 90% by weight of one isomer and 10% by weight or less of its opposite isomer. In a more preferred embodiment, the term means at least a 95:5 mixture.

As used herein, "diastereomeric excess" (abbreviated "de") for diastereomer A refers to the amount of diastereomer A minus the amount of diastereomer B divided by amount of diastereomer A plus the amount of diastereomer B [(A−B)/(A+B)]. For example, when a substance (such as a compound or crystal) is characterized as having 90% de, that means that greater than 95% by weight of the substance is one diastereomer and less than 5% by weight is any other diastereomers.

The graphic representations of racemic, ambiscalemic and scalemic or enantiomerically pure compounds used herein are taken from Maehr, J. Chem. Ed., 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

Iron-Catalyzed Conversion

The methods described herein are not limited to practice on specified enamides characterized by any particular structural element or membership within any single structural class. According, provided are methods of broad applicability across a wide range of enamide structures.

A method for preparing a chiral amine from a ketone is illustrated in the following scheme:

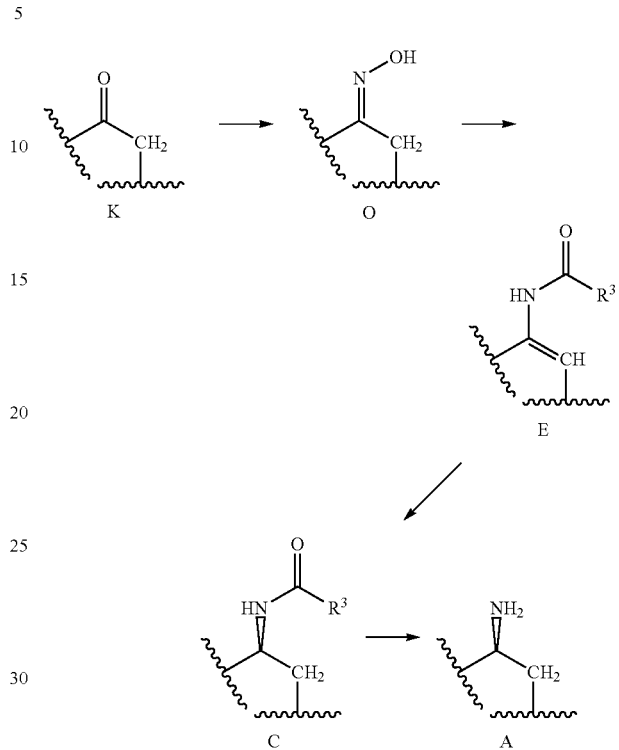

wherein K is a ketone, O is an oxime, E is an enamide, C is a carboxamide, A is an amine, and $R^3$ is the residue of an acyl donor.

Oxime to Enamide

In some embodiments, provided is a method of converting an oxime (O) to an enamide (E):

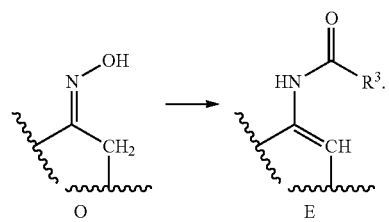

In some embodiments, provided is a method of converting an oxime (O) to an enamide (E):

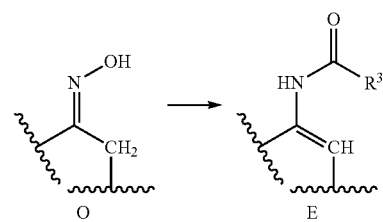

wherein the method comprises contacting the oxime (O) with an acyl donor and a phosphine in the presence of an iron reagent that provides from 10 to 2000 ppm iron.

In another embodiment, provided is a method for converting an oxime to an enamide, the method comprising contacting the oxime with an acyl donor and a phosphine in the presence of an iron reagent that provides from 10 to 2000 ppm iron under conditions that convert the oxime to the enamide.

In some embodiments, provided is a method of converting an oxime (O) to an enamide (E):

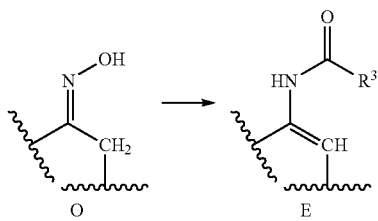

wherein the method comprises contacting the oxime (O) with an acyl donor and a phosphine in the presence of an iron reagent that provides from 10 to 1000 ppm iron.

In another embodiment, provided is a method for converting an oxime to an enamide, the method comprising contacting the oxime with an acyl donor and a phosphine in the presence of an iron reagent that provides from 10 to 1000 ppm iron under conditions that convert the oxime to the enamide.

In some embodiments, provided is a method of converting an oxime (O) to an enamide (E):

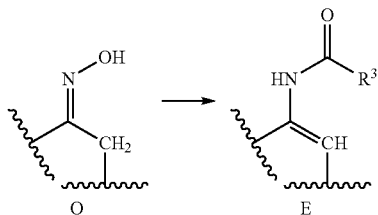

wherein the method comprises contacting the oxime (O) with an acyl donor and a phosphine in the presence of an iron reagent that provides from 1000 to 2000 ppm iron.

In another embodiment, provided is a method for converting an oxime to an enamide, the method comprising contacting the oxime with an acyl donor and a phosphine in the presence of an iron reagent that provides from 1000 to 2000 ppm iron under conditions that convert the oxime to the enamide.

In some embodiments, provided is a method of converting an oxime (O) to an enamide (E):

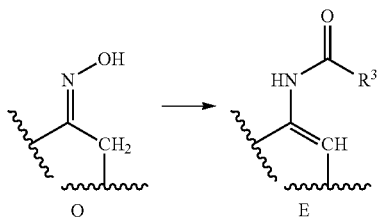

wherein the method comprises contacting the oxime (O) with an acyl donor and a phosphine in the presence of an iron reagent that provides from 1500 to 2000 ppm iron.

In another embodiment, provided is a method for converting an oxime to an enamide, the method comprising contacting the oxime with an acyl donor and a phosphine in the presence of an iron reagent that provides from 1500 to 2000 ppm iron under conditions that convert the oxime to the enamide.

Ketone to Enamide

Provided is a method of converting a ketone (K) to an enamide (E). An advantage of some embodiments described herein is the conversion of the ketone (K) to the enamide (E) in a "single pot." For example, while in some embodiments it may be possible to isolate the oxime (O), it will not be necessary to obtain the enamide (E).

Reacting the ketone (K) with a hydroxylamine may be done in the presence of a base, such as sodium acetate, in a solvent. See, e.g., Sandler and Karo, "ORGANIC FUNCTIONAL GROUP PREPARATIONS," Vol. 3, pp 372-381, Academic Press, New York, 1972. In some embodiments, the ketone (K) may be an aliphatic ketone or arylalkyl ketone (e.g., a naphthalenic ketone), as long as there is at least one proton on an sp3 carbon adjacent the ketone.

In some embodiments, provided is a method of converting a ketone (K) to an enamide (E):

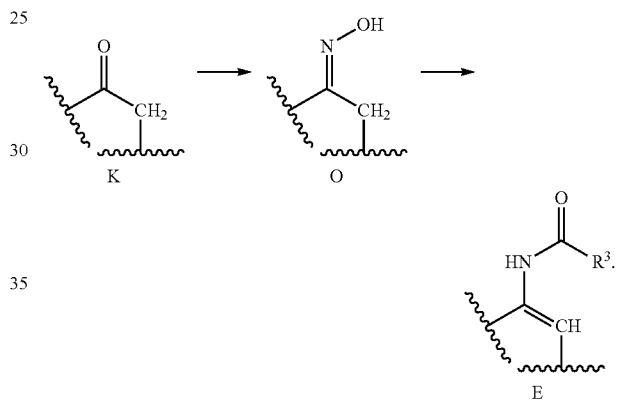

In some embodiments, provided is a method of converting a ketone (K) to an enamide (E):

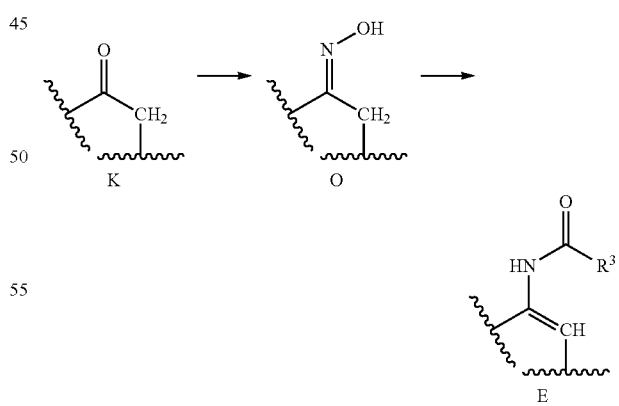

wherein the method comprises
(a) first reacting a ketone with hydroxylamine to provide an oxime; and
(b) second reacting the oxime with an acyl donor and a phosphine in the presence of an iron reagent.

In another embodiment, provided is a method for converting a ketone to an enamide, the method comprising:

9

(a) first reacting the ketone with hydroxylamine to provide an oxime; and
(b) second reacting the oxime with an acyl donor and a phosphine in the presence of an iron reagent that provides from 10 to 2000 ppm iron.

In another embodiment, provided is a method for converting a ketone to an enamide, the method comprising:
(a) first reacting the ketone with hydroxylamine to provide an oxime; and
(b) second reacting the oxime with an acyl donor and a phosphine in the presence of an iron reagent that provides from 10 to 1000 ppm iron.

In another embodiment, provided is a method for converting a ketone to an enamide, the method comprising:
(a) first reacting the ketone with hydroxylamine to provide an oxime; and
(b) second reacting the oxime with an acyl donor and a phosphine in the presence of an iron reagent that provides from 1000 to 2000 ppm iron.

In another embodiment, provided is a method for converting a ketone to an enamide, the method comprising:
(a) first reacting the ketone with hydroxylamine to provide an oxime; and
(b) second reacting the oxime with an acyl donor and a phosphine in the presence of an iron reagent that provides from 1500 to 2000 ppm iron.

In some embodiments, provided is a method of converting a ketone (K) to an enamide (E):

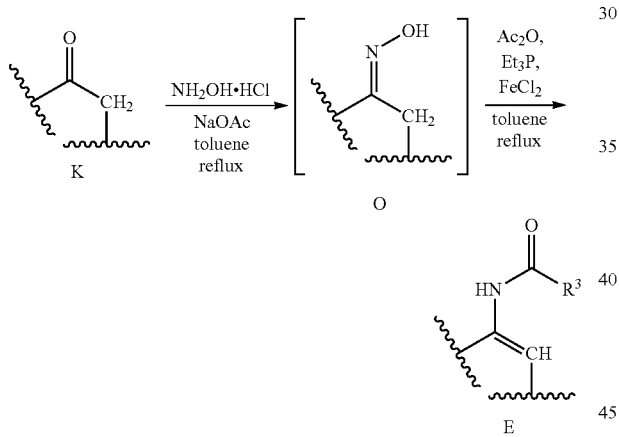

wherein the method comprises
(a) first reacting a ketone with hydroxylamine to provide an oxime; and
(b) second reacting the oxime with an acyl donor and a phosphine in the presence of an iron reagent. In some embodiments, steps (a) and (b) are carried out without isolation of the oxime.

In some embodiments, provided is a method for converting a prochiral ketone (K) to an enantiomerically enriched chiral amide (C):

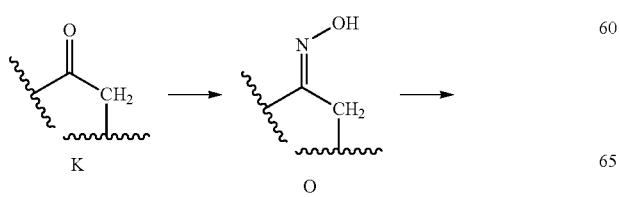

10

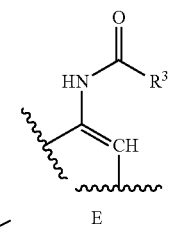

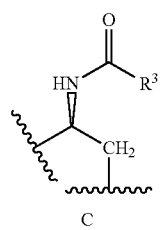

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 10 to 2000 ppm iron to provide an enamide (E); and
(c) third reducing the enamide (E) with hydrogen in the presence of a chiral catalyst to produce an enantiomerically enriched chiral amide (C).

In some embodiments, provided is a method for converting a prochiral ketone (K) to an enantiomerically enriched chiral amide (C):

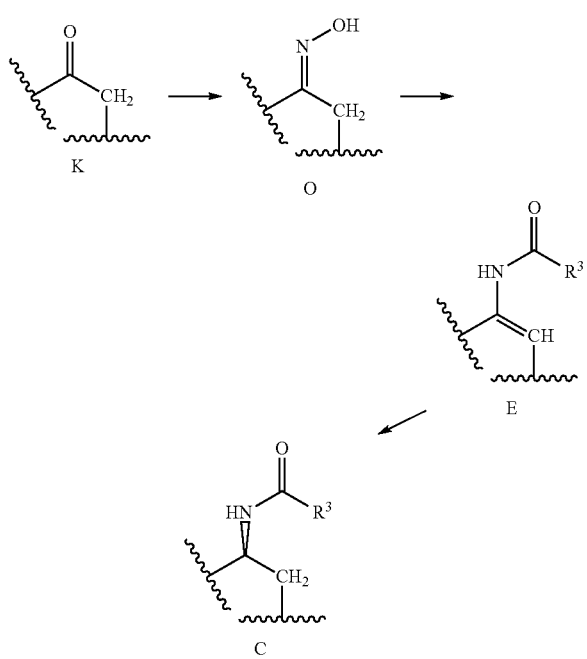

wherein the method comprises:
(a) first reacting the prochiral ketone (K) with hydroxylamine to provide an oxime (O);

(b) second reacting the oxime (O) with an acyl donor and a phosphine in the presence of an iron reagent that provides from 10 to 1000 ppm iron to provide an enamide (E); and
(c) third reducing the enamide (E) with hydrogen in the presence of a chiral catalyst to produce an enantiomerically enriched chiral amide (C).

In some embodiments, provided is a method for converting a prochiral ketone (K) to an enantiomerically enriched chiral amide (C):

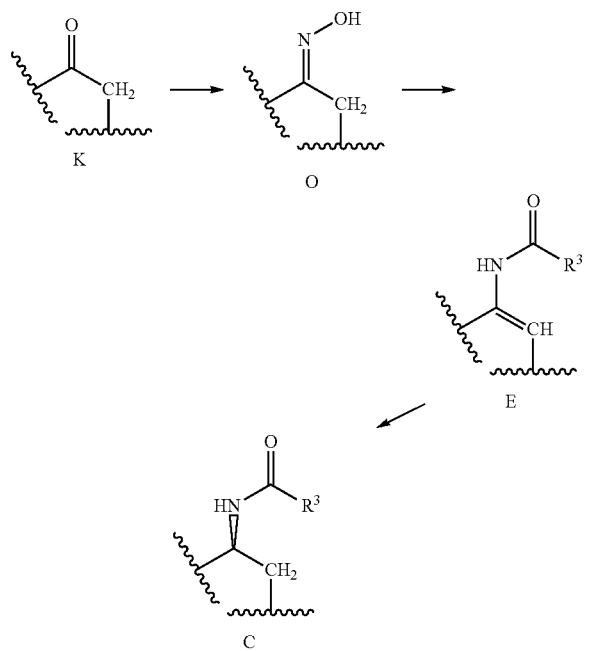

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 1000 to 2000 ppm iron to provide an enamide (E); and
(c) third reducing the enamide (E) with hydrogen in the presence of a chiral catalyst to produce an enantiomerically enriched chiral amide (C).

In some embodiments, provided is a method for converting a prochiral ketone (K) to an enantiomerically enriched chiral amide (C):

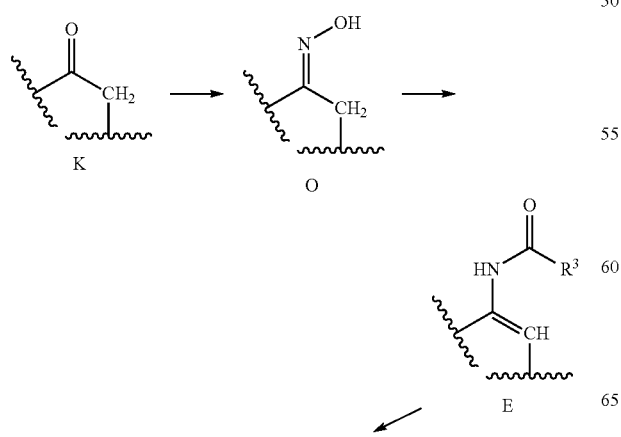
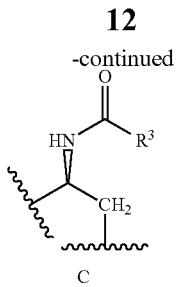

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 1500 to 2000 ppm iron to provide an enamide (E); and
(c) third reducing the enamide (E) with hydrogen in the presence of a chiral catalyst to produce an enantiomerically enriched chiral amide (C).

In some embodiments, provided is a method for converting a prochiral ketone (K) to an enantiomerically enriched chiral amine (A):

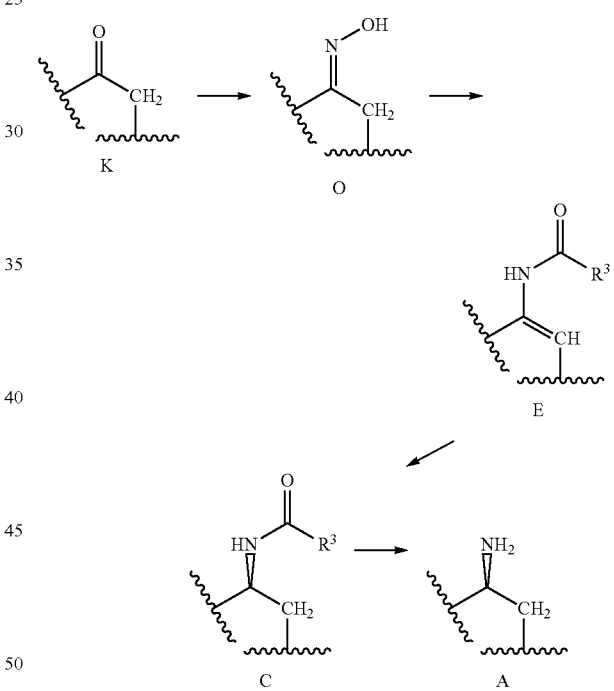

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 10 to 2000 ppm iron to provide an enamide (E);
(c) third reducing the enamide (E) with hydrogen in the presence of a chiral catalyst to produce an enantiomerically enriched chiral amide (C); and
(d) fourth hydrolyzing the enantiomerically enriched chiral amide (C) to an enantiomerically enriched chiral amine (A).

In some embodiments, provided is a method for converting a prochiral ketone (K) to an enantiomerically enriched chiral amine (A):

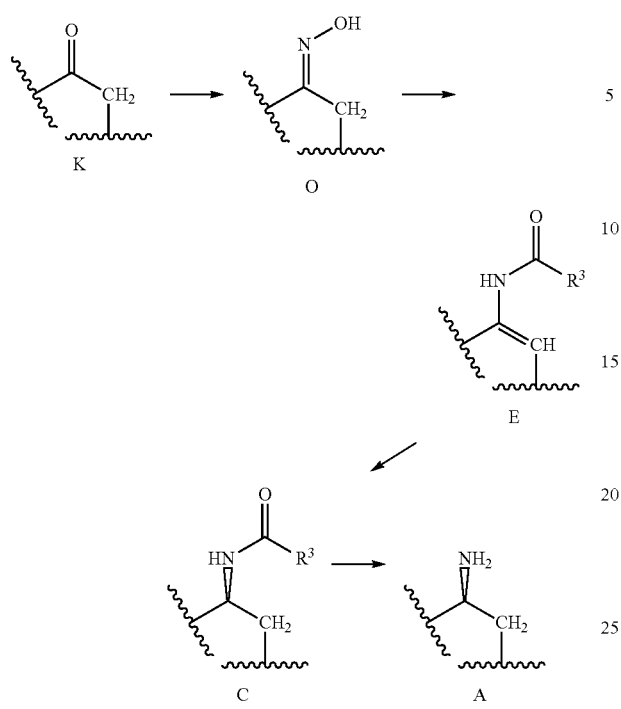

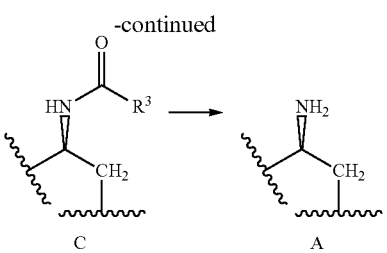

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 1000 to 2000 ppm iron to provide an enamide (E);
(c) third reducing the enamide (E) with hydrogen in the presence of a chiral catalyst to produce an enantiomerically enriched chiral amide (C); and
(d) fourth hydrolyzing the enantiomerically enriched chiral amide (C) to an enantiomerically enriched chiral amine (A).

In some embodiments, provided is a method for converting a prochiral ketone (K) to an enantiomerically enriched chiral amine (A):

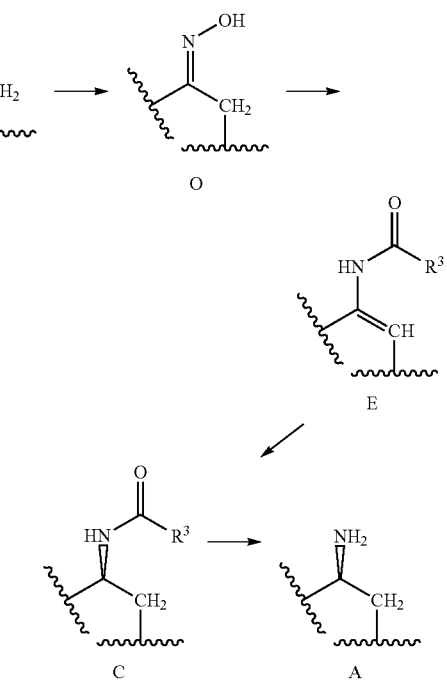

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 10 to 1000 ppm iron to provide an enamide (E);
(c) third reducing the enamide (E) with hydrogen in the presence of a chiral catalyst to produce an enantiomerically enriched chiral amide (C); and
(d) fourth hydrolyzing the enantiomerically enriched chiral amide (C) to an enantiomerically enriched chiral amine (A).

In some embodiments, provided is a method for converting a prochiral ketone (K) to an enantiomerically enriched chiral amine (A):

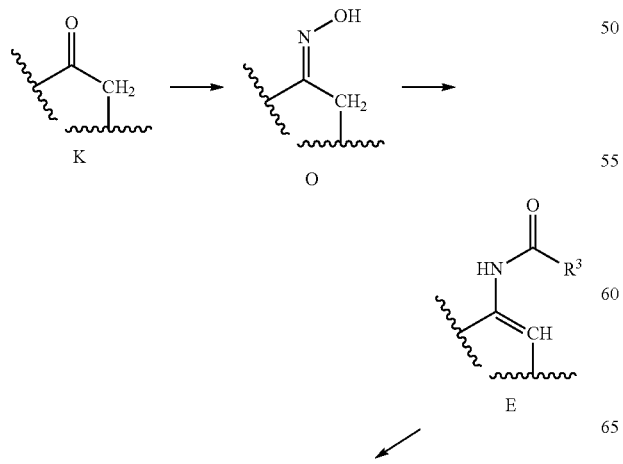

wherein the method comprises:
(a) first reacting the prochiral ketone (K) with hydroxylamine to provide an oxime (O);
(b) second reacting the oxime (O) with an acyl donor and a phosphine in the presence of an iron reagent that provides from 1500 to 2000 ppm iron to provide an enamide (E);

(c) third reducing the enamide (E) with hydrogen in the presence of a chiral catalyst to produce an enantiomerically enriched chiral amide (C); and (d) fourth hydrolyzing the enantiomerically enriched chiral amide (C) to an enantiomerically enriched chiral amine (A).

In some embodiments, provided is a process for preparing amine (A)

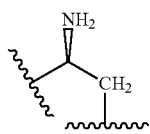

A according to the following general scheme:

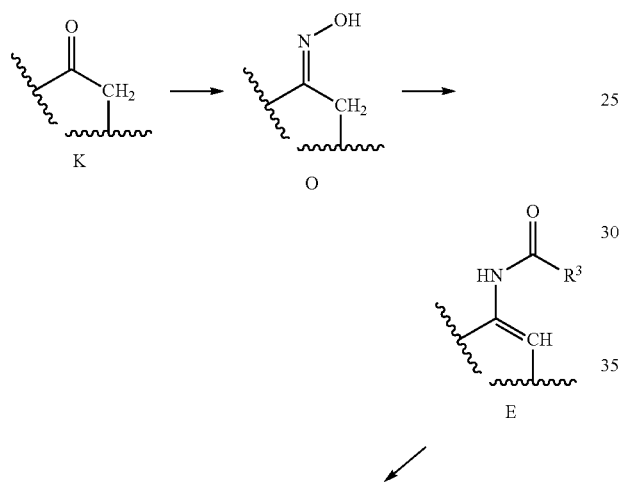

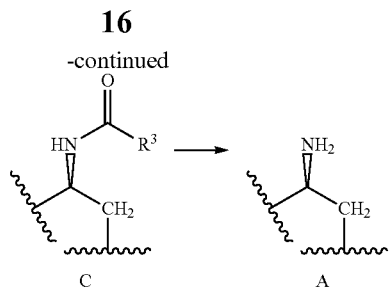

wherein the process comprises reacting the oxime (O) with an acyl donor and a phosphine in the presence of an iron reagent that provides from 10 to 2000 ppm iron to provide an enamide (E). In some embodiments, the iron reagent provides from 10 to 1000 ppm iron. In some embodiments, the iron reagent provides from 1000 to 2000 ppm iron. In some embodiments, the iron reagent provides from 1500 to 2000 ppm iron.

In some embodiments, provided is a process for preparing a compound (6)

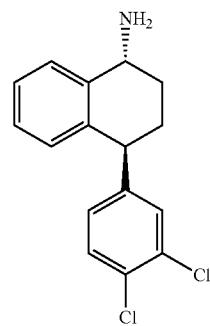

according to the following general scheme:

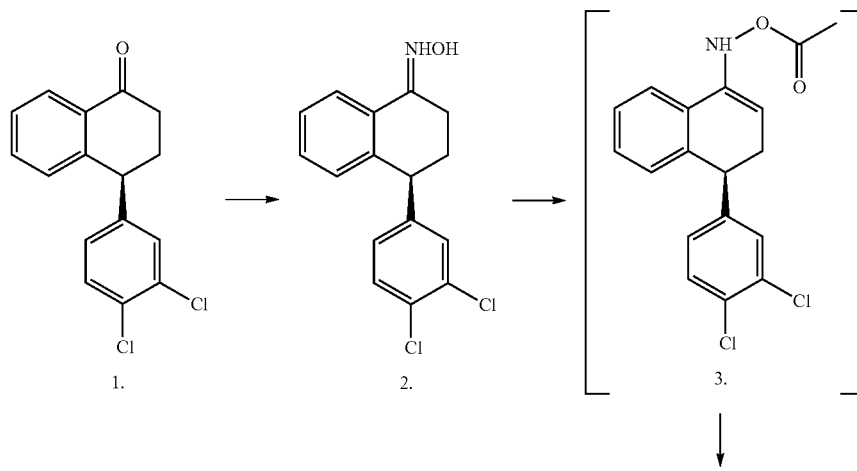

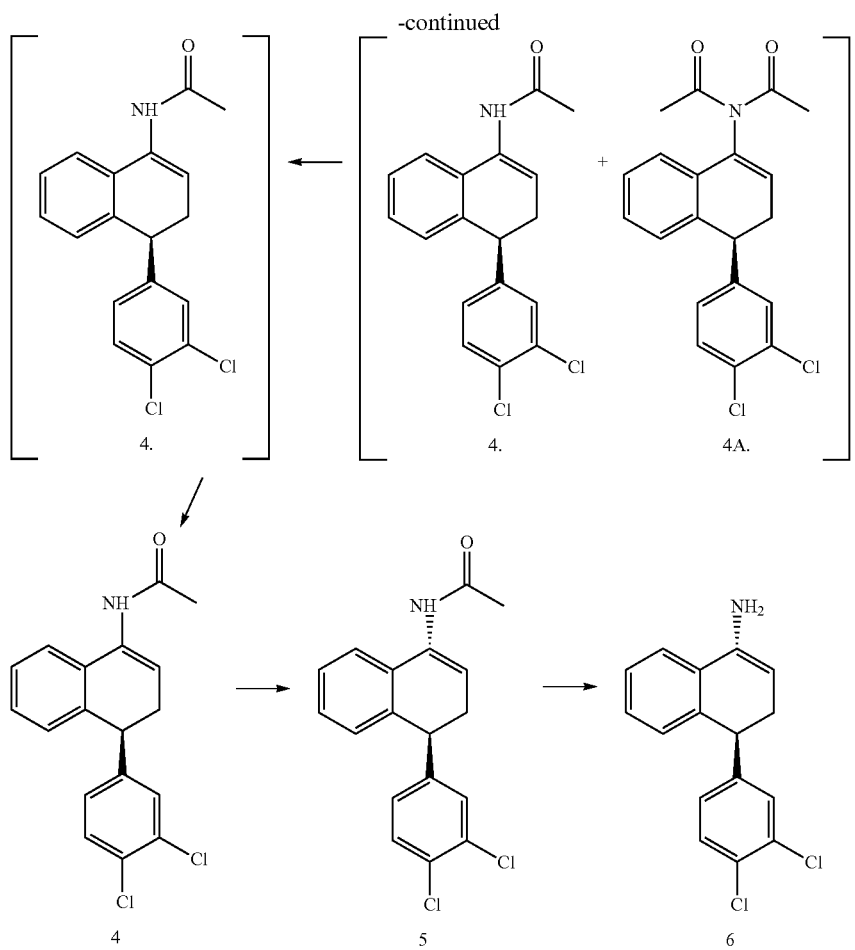

wherein the process comprises reacting the oxime (2) with an acyl donor and a phosphine in the presence of an iron reagent that provides from 10 to 2000 ppm iron to provide an enamide (4). In some embodiments, the iron reagent provides from 10 to 1000 ppm iron. In some embodiments, the iron reagent provides from 1000 to 2000 ppm iron. In some embodiments, the iron reagent provides from 1500 to 2000 ppm iron.

In some embodiments, the enantiomerically enriched chiral amine (C) is substantially optically pure.

In some embodiments, the oxime is an aliphatic ketone oxime. In some embodiments, the oxime is a tetralone oxime. In some embodiments, the oxime is

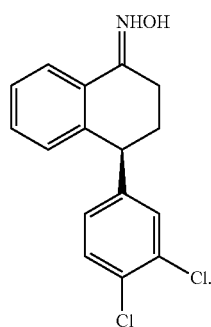

In some embodiments, the amine is

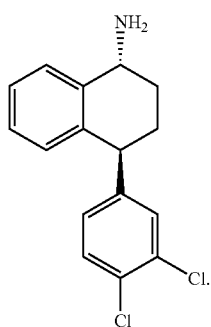

In some embodiments, provided is a method of accelerating the conversion of an oxime to an enamide comprising a method described herein. In some embodiments, provided is a method of accelerating the conversion of a ketone to an enamide comprising a method described herein.

In some embodiments, provided herein is a method for converting an oxime to an enamide, the process comprising contacting the oxime with an acyl donor and a phosphine in the presence of an iron reagent that provides from 10 to 2000 ppm iron under conditions that convert the oxime to the enamide.

In some embodiments, provided herein is a method for converting a ketone to an enamide, the process comprising the sequential steps of:

(a) reacting the ketone with hydroxylamine to provide an oxime; and
(b) reacting the oxime with an acyl donor and a phosphine in the presence of an iron reagent that provides from 10 to 2000 ppm iron.

In some embodiments, provided herein is a method for converting a prochiral ketone to an enantiomerically enriched chiral amide, the process comprising:
(a) reacting the ketone with hydroxylamine to provide an oxime;
(b) reacting the oxime with an acyl donor and a phosphine in the presence of an iron reagent that provides from 10 to 2000 ppm iron to provide an enamide; and
(c) reducing the enamide with hydrogen in the presence of a chiral catalyst to produce an enantiomerically enriched chiral amide.

In some embodiments, provided herein is a method for converting a prochiral ketone to an enantiomerically enriched chiral amine, the process comprising:
(a) reacting the ketone with hydroxylamine to provide an oxime;
(b) reacting the oxime with an acyl donor and a phosphine in the presence of an iron reagent that provides from 10 to 2000 ppm iron to provide an enamide;
(c) reducing the enamide with hydrogen in the presence of a chiral catalyst to produce an enantiomerically enriched chiral amide; and
(d) hydrolyzing the chiral amide to an enantiomerically enriched chiral amine.

In some embodiments, provided is the method as described in any one or more of the preceding four paragraphs wherein the acyl donor is acetic anhydride.

In some embodiments, provided is the method as described in any one or more of the preceding five paragraphs wherein the phosphine is chosen from tri n-butylphosphine, triethyl phosphine, diphenylphosphinoethane and triphenyl phosphine.

In some embodiments, provided is the method as described in any one or more of the preceding six paragraphs wherein the phosphine is triethyl phosphine.

In some embodiments, provided is the method as described in any one or more of the preceding seven paragraphs wherein the iron reagent is chosen from elemental iron and Fe(II) salts and Fe(III) salts wherein the counter ion is halide or alkanoate.

In some embodiments, provided is the method as described in any one or more of the preceding eight paragraphs wherein the iron reagent is chosen from $FeCl_2$ and $Fe(OAc)_2$.

In some embodiments, provided is the method as described in any one or more of the preceding nine paragraphs wherein the iron reagent provides from 10 to 2000 ppm iron.

In some embodiments, provided is the method as described in any one or more of the preceding ten paragraphs wherein the iron reagent provides from 10 to 1900 ppm iron.

In some embodiments, provided is the method as described in any one or more of the preceding eleven paragraphs wherein the iron reagent provides from 10 to 1800 ppm iron.

The invention further relates to a process as described in any one or more of the preceding twelve paragraphs wherein the iron reagent provides from 25 to 1800 ppm iron.

In some embodiments, provided is the method as described in any one or more of the preceding thirteen paragraphs wherein the iron reagent provides from 50 to 1800 ppm iron.

In some embodiments, provided is the method as described in any one or more of the preceding fourteen paragraphs wherein the iron reagent provides from 100 to 1800 ppm iron.

In some embodiments, provided is the method as described in any one or more of the preceding fifteen paragraphs wherein the iron reagent provides from 200 to 1700 ppm iron.

The invention further relates to a process as described in any one or more of the first twelve of the preceding sixteen paragraphs wherein the iron reagent provides from 10 to 100 ppm iron.

In some embodiments, provided is the method as described in any one or more of the first twelve of the preceding seventeen paragraphs wherein the iron reagent provides from 10 to 50 ppm iron.

In some embodiments, provided is the method as described in any one or more of the first twelve of the preceding eighteen paragraphs wherein the iron reagent provides from 25 to 100 ppm iron.

In some embodiments, provided is the method as described in any one or more of the first twelve of the preceding nineteen paragraphs wherein the iron reagent provides from 50 to 200 ppm iron.

In some embodiments, provided is the method as described in any one or more of the preceding twenty paragraphs wherein the process is carried out in a solvent at a temperature between 80° C. and 150° C.

In some embodiments, provided is the method as described in any one or more of the preceding twenty-one paragraphs wherein the solvent is toluene.

In some embodiments, provided is the method as described in any one or more of the preceding twenty-two paragraphs wherein the oxime is an aliphatic ketone oxime.

In some embodiments, provided is the method as described in any one or more of the preceding twenty-three paragraphs wherein the oxime is a tetralone oxime.

In some embodiments, provided is the method as described in any one or more of the preceding twenty-three paragraphs wherein steps (a) and (b) are carried out without isolation of the oxime.

In some embodiments, provided is the method as described in any one or more of the preceding twenty-four paragraphs wherein the acyl donor is acetic anhydride, the phosphine is triethyl phosphine and the iron reagent is chosen from $FeCl_2$ and $Fe(OAc)_2$.

In some embodiments, provided is the method as described in any one or more of the preceding twenty-six paragraphs wherein the oxime is

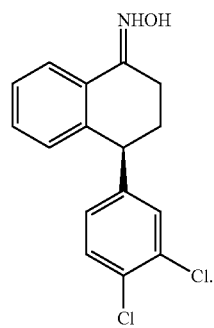

In some embodiments, provided is the method as described in any one or more of the first twenty-two of the preceding twenty-five paragraphs wherein the amine is

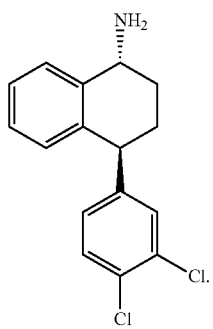 [SMILES: N[C@@H]1CC[C@@H](c2ccc(Cl)c(Cl)c2)c2ccccc21]

In one embodiment of these processes relating to the foregoing oxime and amine, the acyl donor is acetic anhydride, the phosphine is triethyl phosphine, and the iron reagent is $FeCl_2$ and/or $Fe(OAc)_2$.

Exemplary reagents and reaction conditions for the conversion of an enamide to an amide are set forth in PCT application WO 2007/115185, which is hereby incorporated by reference in its entirety.

Catalysts

In some embodiments, the methods described herein for reducing an enamide (E) to an amide (e.g., enantiomerically enriched chiral amide (C)) includes contacting the enamide (E) with a hydrogenation catalyst and hydrogen or a hydrogen transfer reagent under conditions appropriate to hydrogenate the carbon-carbon double bond of the enamide (E). In some embodiments, the enamide substrate is chiral or prochiral and the reduction is performed in a stereoselective manner. In some embodiments, the catalyst is a chiral catalyst. In some embodiments, the chiral catalyst is a transition metal catalyst. In some embodiments, the catalyst is a transition metal catalyst.

Chiral transition metal complex catalysts may be used in catalytic asymmetric hydrogenation reactions. For example, transition metal complexes of ruthenium, iridium, rhodium, palladium, nickel or the like, which contain optically active phosphines as ligands, have performed as catalysts for asymmetric synthetic reactions, and/or are used in industrial application. See, e.g., ASYMMETRIC CATALYSIS IN ORGANIC SYNTHESIS, Ed., R. Noyori, Wiley & Sons (1994); and G. Franck), et al., *Angewandte Chemie. Int. Ed.*, 39: 1428-1430 (2000). In some embodiments, the metal in the catalyst is rhodium (Rh), ruthenium (Ru) or iridium (Ir).

In some embodiments, the hydrogenation catalyst is a chiral complex of a transition metal with a chiral phosphine ligand, including monodentate and bidentate ligands. For example, bidentate ligands include 1,2-bis(2,5-dimethylphospholano)ethane (MeBPE), P,P-1,2-phenylenebis{(2,5-endo-dimethyl)-7-phosphabicyclo[2.2.1]heptane} (MePennPhos), 5,6-bis(diphenylphosphino) bicyclo[2.2.1]hept-2-ene (NorPhos) and 3,4-bis(diphenylphosphino) N-benzyl pyrrolidine (commercially available as catASium® D).

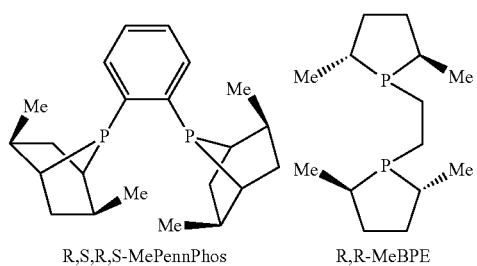

R,S,R,S-MePennPhos     R,R-MeBPE

-continued

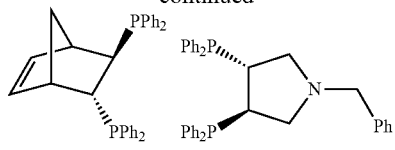

R,R-NorPhos     R,R-catASium® D

In some embodiments, the chiral catalyst is (R,S,R,S)-MePennPhos(COD)RhBF$_4$, (R,R)-MeBPE(COD)RhBF$_4$, (R,R)-NorPhos(COD)RhBF$_4$ (Brunner et al., *Angewandte Chemie* 91(8): 655-6 (1979)), or (R,R)-catASium® D(COD)RhBF$_4$ (Nagel et al., *Chemische Berichte* 119(11): 3326-43 (1986)).

A catalyst may be present in the reaction mixture in any useful amount. In some embodiments, the catalyst is present in an amount of from about 0.005 mol % to about 1 mol %. In some embodiments the catalyst is present in an amount of from about 0.01 mol % to about 0.5 mol %. In some embodiments the catalyst is present in an amount of from about 0.02 mol % to about 0.2 mol %.

Deacylating Reagents

Some methods of deacylating amides to the corresponding amines are known in the art. In some embodiments, a deacylating reagent is used to hydrolyze the amide to the corresponding amine. In some embodiments, the deacylating reagent is an enzyme. Exemplary enzymes of use in this process include those of the class EC 3.5.1 (e.g., amidase, aminoacylase), and EC 3.4.19.

In another embodiment, the deacylating reagent is an acid or a base. The acid or base can be either inorganic or organic. Mixtures of acids or mixtures of bases are useful as well. When the deacylating reagent is an acid, it is generally preferred that the acid is selected so that the acid hydrolysis produces a product that is a salt form of the amine. In some embodiments, the acid is hydrochloric acid (HCl).

Other deacylating conditions of use in the present invention include, but are not limited to, methanesulfonic acid/HBr in alcoholic solvents, triphenylphosphite/halogen (e.g., bromine, chlorine) complex and a di-t-butyl dicarbonate/lithium hydroxide sequence.

In some cases, the amide is deacylated by treatment with an activating agent, e.g., trifluoromethanesulfonic anhydride, phosgene, and preferably, oxalyl chloride/pyridine. The reaction is quenched with an alcohol, often a glycol, such as propylene glycol.

Phosphorus Reagents

A phosphorus reagent (e.g., a phosphine) may be incorporated into the reaction mixture in substantially any useful amount. In some embodiments, reactions utilize from about 0.5 equivalents to about 5 equivalents of the phosphorus reagent with respect to the carbonyl-containing substrate. In some embodiments, reactions utilize from about 1 equivalent to about 3 equivalents of the phosphorus reagent with respect to the carbonyl-containing substrate. In some embodiments, reactions utilize from about 1.1 equivalents to about 2 equivalents of the phosphorus reagent with respect to the carbonyl-containing substrate.

Iron Reagents

The iron reagent may be elemental iron, or it may be an Fe(II) or Fe(III) salt in which the counter ion is halide or alkanoate. Ferrous chloride, ferrous acetate, ferric chloride, and ferric acetate have the advantage of being convenient to handle and may be added to the reaction mixture as a solution or suspension. In some embodiments, the iron reagent should provide from 10 to 1000 ppm iron, based on weight of iron in the iron source to weight of the ketone. In some embodiments, the iron reagent should provide from 10 to 2000 ppm iron, based on weight of iron in the iron source to weight of the ketone. In some embodiments, the iron reagent should provide from 1000 to 2000 ppm iron, based on weight of iron in the iron source to weight of the ketone. In some embodiments, the iron reagent should provide from 1500 to 2000 ppm iron, based on weight of iron in the iron source to weight of the ketone. So for example, for a 100 g ketone reaction, 50 ppm equates to 18 mg of $FeCl_2\text{-}4H_2O$ (ferrous chloride tetrahydrate being 28% iron by weight). Possible ranges, in ppm, for the iron reagent are 10-50, 10-100, 10-200, 10-250, 10-400, 10-500, 10-700, 10-800, 10-1000, 25-50, 25-100, 25-200, 25-250, 25-400, 25-500, 25-700, 25-800, 25-1000, 40-100, 40-200, 40-250, 40-400, 40-500, 40-700, 40-800, 40-1000, 50-100, 50-200, 50-250, 50-400, 50-500, 50-700, 50-800, and 50-1000. Possible ranges, in ppm, for the iron reagent are 10-2000, 50-2000, 100-2000, 150-2000, 200-2000, 250-2000, 300-2000, 350-2000, 400-2000, 450-2000, 500-2000, 550-2000, 600-2000, 650-2000, 700-2000, 750-2000, 800-2000, 850-2000, 900-2000, 950-2000, 1000-2000, 1050-2000, 1100-2000, 1150-2000, 1200-2000, 1250-2000, 1300-2000, 1350-2000, 1400-2000, 1450-2000, 1500-2000, 1550-2000, 1600-2000, 1650-2000, 1700-2000, 1750-2000, 1800-2000, 1850-2000, 1900-2000, and 1950-2000.

In some embodiments, the iron reagent is elemental iron, an Fe(II) salt, or an Fe(III) salt wherein the counter ion is halide or alkanoate. In some embodiments, the iron reagent is $FeCl_2$ or $Fe(OAc)_2$. In some embodiments, the iron reagent is $FeCl_2$ and $Fe(OAc)_2$. In some embodiments, the iron reagent is $FeCl_2$. In some embodiments, the iron reagent is $Fe(OAc)_2$.

In some embodiments, the iron reagent provides from 10 to 2000 ppm iron. In some embodiments, the iron reagent provides from 10 to 1000 ppm iron. In some embodiments, the iron reagent provides from 1000 to 2000 ppm iron. In some embodiments, the iron reagent provides from 1500 to 2000 ppm iron. In some embodiments, the iron reagent provides from 10 to 100 ppm iron. In some embodiments, the iron reagent provides from 10 to 50 ppm iron. In some embodiments, the iron reagent provides from 25 to 100 ppm iron. In some embodiments, the iron reagent provides from 50 to 200 ppm iron.

The methods disclosed herein may, under normal circumstances in which the oxime contains less than 10 ppm of iron, involve a step of adding a solution or suspension of the appropriate iron reagent to the oxime, either before, after, or concurrent with, the addition of one or both of the other components (acyl donor and phosphine).

Methods described herein may typically be carried out in a solvent at a temperature between about 80° C. and about 150° C. A process described herein below about 80° C. may still work, and there may be occasion when the stability of the oxime will dictate a lower temperature, but on most occasions, time will be saved by running the reaction above 80° C. Correspondingly, a reaction could be run at temperatures above 150° C., but many reactants and products are not stable at such high temperatures and thus the purity of the product may be compromised above 150° C. To achieve temperatures in the desired range, the preferred solvents will be inert solvents, typically aprotic solvents, having a boiling point between 80° C. and 150° C. A solvent that fits these criteria is toluene. Others include chlorobenzene, xylene, acetonitrile and dioxane.

In some embodiments, a method described herein is carried out in a solvent at a temperature between about 80° C. and about 150° C. In some embodiments, a method described herein is carried out in a solvent at a temperature between 80° C. and 150° C.

In some embodiments, the solvent is toluene, chlorobenzene, xylene, acetonitrile or dioxane. In some embodiments, the solvent is toluene. In some embodiments, the solvent is chlorobenzene. In some embodiments, the solvent is xylene. In some embodiments, the solvent is acetonitrile. In some embodiments, the solvent is dioxane.

In some embodiments, the acyl donor is acetic anhydride, the phosphine is triethyl phosphine and the iron reagent is $FeCl_2$ or $Fe(OAc)_2$. In some embodiments, the acyl donor is acetic anhydride, the phosphine is triethyl phosphine and the iron reagent is $FeCl_2$ and $Fe(OAc)_2$. In some embodiments, the acyl donor is acetic anhydride, the phosphine is triethyl phosphine and the iron reagent is $FeCl_2$. In some embodiments, the acyl donor is acetic anhydride, the phosphine is triethyl phosphine and the iron reagent is $Fe(OAc)_2$.

In some embodiments, provided are methods for the conversion of oximes to the corresponding enamides in which only catalytic quantities of metal are required. In some embodiments, the enamides are formed in high yields and purities. The process may be amenable to large-scale production. Exemplary conditions are set forth below for oximes of formula

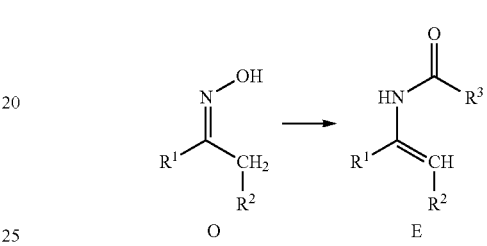

wherein $R^1$, $R^2$, and $R^3$ are hydrocarbyl residues or substituted hydrocarbyl residues.

In some embodiments, an optically pure tetralone (1) is converted into the corresponding oxime (2) and then to the enamide (4):

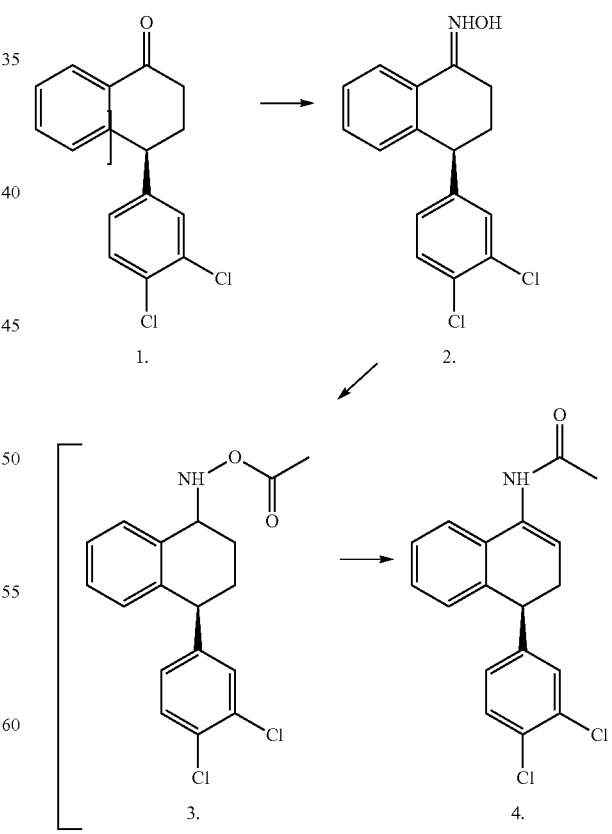

wherein optically pure tetralone (1) is treated with hydroxylamine hydrochloride, and sodium acetate in methanol, toluene or a mixture of the two, to afford the oxime (2). The oxime (2) can either be isolated or carried forward as a solution in a suitable solvent to the next step.

Acylation of the oxime (2) (e.g., using an acyl donor such as acetic anhydride) affords the O-acetyloxime intermediate (3). It is thought that one electron reduction of the O-acetyloxime gives the imine radical, which then undergoes a second one-electron reduction to generate the iminium anion. Next, acylation of the iminium anion with a second equivalent of acetic anhydride, followed by tautomerization leads to the enamide (4).

In some embodiments, the enamide (4) is converted to an amide (5):

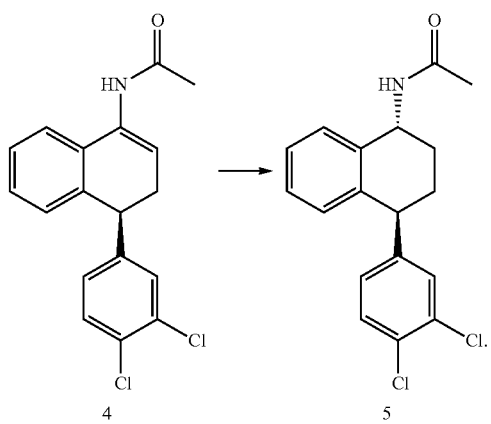 [SMILES: CC(=O)NC1=CC[C@@H](c2ccc(Cl)c(Cl)c2)c2ccccc21 ; CC(=O)N[C@@H]1CC[C@@H](c2ccc(Cl)c(Cl)c2)c2ccccc21]

When using rhodium catalyst systems based on chiral bidentate ligands, such as those derived from 1,2-bis(phospholano)ethane (BPE) ligands, P,P-1,2-phenylenebis(7-phosphabicyclo[2.2.1]heptane) (PennPhos) ligands, 5,6-bis(phosphino)bicyclo[2.2.1]hept-2-ene (NorPhos) ligands, or 3,4-bis(phosphino) pyrrolidine (commercially available as catASium® D) ligands, the diastereomeric purity of the trans amide derived from the corresponding enamide is high. In some embodiments, the enamide (4) is hydrogenated at about 4 to about 6 bar hydrogen pressure using about 0.03 to about 0.05 mol % of a Rh-Me-BPE catalyst in isopropanol, to give the trans N-acetyl amide (5) in greater than 95% de.

In some embodiments, the enamide (4) is hydrogenated at about 4 to about 5 bar hydrogen pressure, using about 0.2 to about 0.5 mol % of a Rh-PennPhos catalyst in isopropanol, to give the trans N-acetyl amide (5) in at least 95% de.

In some embodiments the enamide (4) is hydrogenated at about 5 to about 8 bar hydrogen pressure, using about 0.01 to about 0.05 mol % of (R,R)NorPhos(COD)RhBF$_4$ catalyst in isopropanol to give the trans N-acetyl amide (5) in at least 95% de.

The stereoisomerically enriched amide may be purified, or further enriched, by methods known in the art, e.g., chiral chromatography, selective crystallization and the like. Amide (5) has been purified by selective crystallization to about 99% de.

N-Deacylation of (5) affords trans 4-(3,4-dichlorophenyl)-1,2,3,4-tetrahydro-1-naphthalenamine (6), which although depicted below as the free base, is usually recovered as a salt of the acid in which the hydrolysis was carried out.

The method is particularly useful for the large-scale synthesis of bioactive species, such as sertraline and sertraline analogs, and the trans isomers of sertraline, norsertraline and analogs thereof. Sertraline, (1S,4S)-cis 4-(3,4-dichlorophenyl)-1,2,3,4-tetrahydro-N-methyl-1-naphthalenamine, is approved for the treatment of depression by the United States Food and Drug Administration, and is available under the trade name ZOLOFT® (Pfizer Inc., NY, N.Y., USA). (1R,4S)-trans 4-(3,4-Dichlorophenyl)-1,2,3,4-tetrahydro-1-naphthalenamine, colloquially known as transnorsertraline or dasotraline, is currently in clinical trials for ADHD. Thus, a commercial scale process that converts commercially available achiral ketones to their corresponding chiral amines with high enantioselectivity is of great value.

Compounds and Intermediates (S)—N-acetyl-N-(4-(3,4-dichlorophenyl)-3,4-dihydronaphthalen-1-yl)acetamide. In some embodiments, provided is the compound:

Examples

The following examples are for the purpose of illustrating embodiments, and are not to be construed as limiting the scope of this disclosure in any way. The reactants used in the examples below may be obtained either as described herein, or if not described herein, are themselves either commercially available or may be prepared from commercially available materials by methods known in the art.

A. Synthesis of (1R,4S)-4-(3,4-dichlorophenyl)-1,2,3,4-tetrahydronaphthalen-1-amine hydrochloride (6)

Synthesis of Oxime (2)

A suspension formed from a mixture of (S)-tetralone (1) (56.0 g, 0.192 mol), hydroxylamine hydrochloride (14.7 g, 0.212 mol), and sodium acetate (17.4 g, 0.212 mol) in methanol (168 mL) was heated to reflux for 1 to 5 hours under a $N_2$ atmosphere. The progress of the reaction was monitored by HPLC. After the reaction was complete, the reaction mixture was concentrated in vacuo. The residue was diluted with toluene (400 mL) and 200 mL water. The organic layer was separated and washed with an additional 200 mL water. The organic layer was concentrated and dried to give crude solid oxime (2) (58.9 g, 100%), m. p. 117-120° C. $^1$H NMR (400 MHz, $CDCl_3$) δ (ppm) 9.17 (br, 1H, OH), 7.98 (m, 1H), 7.36 (d, 1H, J=8.0 Hz), 7.29 (m, 2H), 7.20 (d, 1H, J=2.4 Hz), 6.91 (m, 2H), 4.11 (dd, 1H, J=7.2 Hz, 4.4 Hz), 2.82 (m, 2H), 2.21 (m, 1H), 2.08 (m, 1H). $^{13}$C NMR (100 MHz, $CDCl_3$) δ 154.94, 144.41, 140.40, 132.83, 130.92, 130.82, 130.68, 130.64, 129.98, 129.38, 128.12, 127.64, 124.48, 44.52, 29.51, 21.27.

Synthesis of Enamide (4) (N—((S)-4-(3,4-dichlorophenyl)-3,4-dihydronaphthalen-1-yl)acetamide)

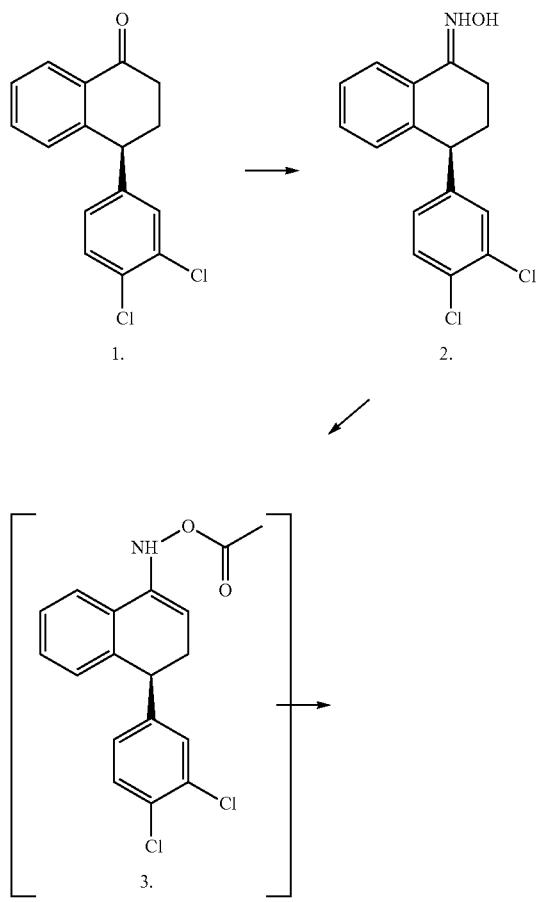

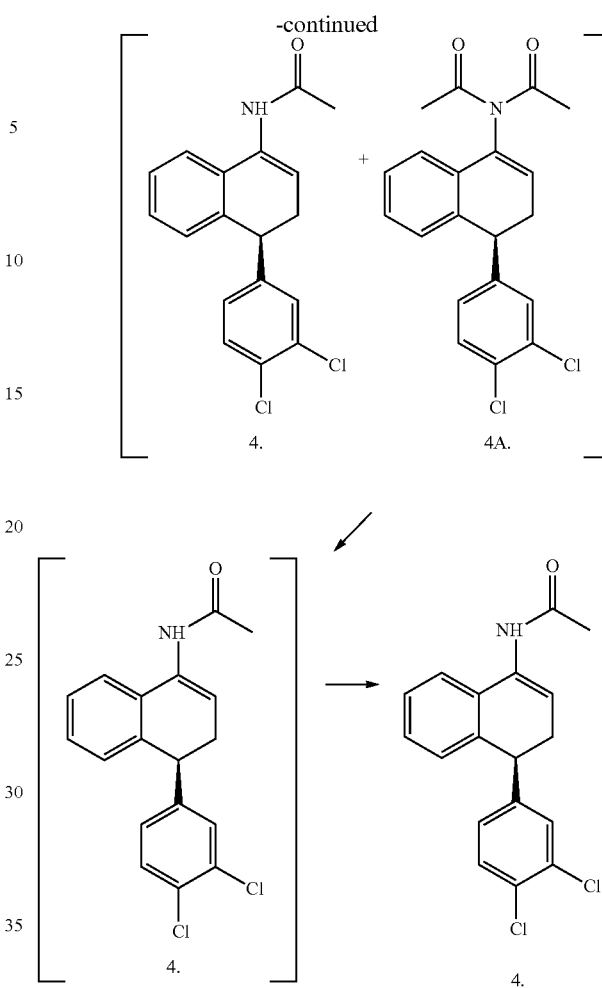

The enamide (4) may be made from ketone (1) without isolation of the above intermediate oxime (2) by acylating in situ to afford the O-acetyloxime intermediate (3), which undergoes reductive acylation to provide a mixture of the enamide (4) and a diacylated enamine (4A). The reaction is carried out in either toluene or o-xylene at reflux. The mixture of (4) and (4A) may then treated with an aqueous solution of base such as sodium hydroxide or sodium carbonate, with or without a phase transfer catalyst (e.g. tetrabutylammonium hydrogen sulfate/hydroxide), to convert the diacylated enamine (4A) to the desired enamide (4).

To a 1-liter, 3-neck round bottom flask equipped with an overhead stirrer, temperature probe and a reflux condenser was added 50.0 grams (172 mmol) of ketone (1), 14.3 g (206 mmol) of hydroxylamine HCl, 16.9 g (206 mmol) of sodium acetate, 7 g of methanol and 175 g of toluene. The mixture was heated to reflux (~80° C.) for 2 h. After 2 h, the mixture was cooled to 20-25° C., and 100 g of DI water was added. The solution was transferred to a 500 mL separatory funnel. The lower aqueous layer was drained and discarded. The organic layer was washed with 100 g of DI water. The lower aqueous layer was drained and discarded. The resulting organic layer was transferred to a 500 mL, 3-neck round bottom flask equipped with an overhead stirrer, temperature probe and a reflux condenser fitted with a 20 mL Dean-Stark receiver with a PTFE stopcock. Next, 0.5 mL of a 1.78 wt % aq. $FeCl_2$ solution was added (prepared by dissolving 454 mg of $FeCl_2.4H_2O$ in 25.4 g of DI water). The solution was heated to reflux and stirred for 1 h to remove water. The solution was then distilled and 112 g of distillate was collected. The solution was then cooled to 60-65° C. and 19.2 g (188 mmol) of acetic anhydride and 22.3 g (189 mmol) of triethylphosphine were added. Caution: Triethylphosphine is pyrophoric and should be handled with extreme care. The Dean-Stark receiver was removed at this point. The solution was slowly heated to reflux and stirred for 2 h. After 2 h, the solution was cooled to 20-25° C., and 106 g of 6N NaOH and 1.7 g of tetrabutylammonium hydroxide (1M solution in MeOH) was added. The biphasic mixture was stirred at 25-30° C. for 1 h with vigorous mixing. The solution was then transferred to a 500 mL separatory funnel. The lower aqueous layer was drained and discarded. The organic layer was transferred to a 1-liter, 3-neck jacketed round bottom flask (with bottom drain-valve) equipped with an overhead stirrer, temperature probe and a reflux condenser. To the solution was added 100 g of toluene, followed by 150 g of 1 wt % aq. acetic acid. The slurry was heated to 65-70° C. to achieve dissolution of the product. The lower aqueous layer was drained and discarded. The organic layer was washed with DI water (3×100 g) at 65-70° C. then transferred to 1-liter, 3-neck round bottom flask equipped with an overhead stirrer, temperature probe and a reflux condenser fitted with a 20 mL Dean-Stark receiver with a PTFE stopcock. Next, 55 g of toluene was added. The solution was heated to reflux and stirred for 2 h to remove water. After 2 h, the solution was then distilled and 57 g of distillate was collected. The solution was cooled to 80° C. and was polish-filtered through a 150 mL filter funnel (pre-coated with 10 g of Celite™ 545 filter aid) into a clean 1-liter, 3-neck round bottom flask equipped with an overhead stirrer, temperature probe and a reflux condenser fitted with a 20 mL Dean-Stark receiver with a PTFE stopcock. The flask and filter were rinsed with 64 g of toluene (~70° C.). The mixture was heated to reflux and the solution was distilled to a volume of approx. 205 mL. A total of 149 g of distillate was collected. The solution was cooled to 60° C. at which point the enamide (4) began to crystallize and a slurry formed. The slurry was cooled to 50° C. and 70 g of n-heptane was added over 60 minutes. The slurry was cooled to 20-25° C. and filtered. The product was washed with 186 g of 28 wt % n-heptane in toluene. The wet-cake was dried in a vacuum oven overnight at 45° C. to yield 50.8 g (89% yield) of enamide (4) as a white solid (>99% purity by HPLC).

$^1$H NMR (400 MHz, CDCl$_3$) δ (ppm) 7.35 (d, 1H, J=8.4 Hz), 7.26 (m, 3H), 7.17 (m, 1H), 7.05 (dd, 1H, J=8.0, 1.6 Hz), 7.00 (br, 1H), 6.87 (m, 0.82H, 82% NH rotamer), 6.80 (br, 0.18H, 18% NH rotamer), 6.31 (t, 0.82H, J=4.8 Hz, 82% H rotamer), 5.91 (br, 0.18H, 18% H rotamer), 4.12 (br, 0.18H, 18% H rotamer), 4.03 (t, 0.82H, J=8.0 Hz, 82% H rotamer), 2.72 (m, 1H), 2.61 (ddd, 1H, J=16.8, 8.0, 4.8 Hz), 2.17 (s, 2.46H, 82% CH$_3$ rotamer), 1.95 (s, 0.54H, 18% CH$_3$ rotamer). 100 MHz $^{13}$C NMR (CDCl$_3$) δ 169.3, 143.8, 137.7, 132.3, 131.8, 131.4, 130.5, 130.3, 130.2, 128.8, 128.1, 127.8, 127.2, 123.8, 122.5, 121.2, 117.5, 42.6, 30.3, 24.1.

Synthesis of (1R,4S)-acetamide (5) (N-((1R,4S)-4-(3,4-dichlorophenyl)-1,2,3,4-tetrahydronaphthalen-1-yl)acetamide)

The enamide (4) (24 g, 72 mmol) was slurried in degassed isopropanol (200 mL). The resulting slurry was transferred to the appropriate reactor. Prior to the addition of the catalyst solution, the content of the reactor was purged with nitrogen. A solution of (R,R)-MeBPE(COD)RhBF$_4$ catalyst (20.1 mg, 0.036 mmol, 0.05 mol %) in isopropanol (IPA) (100 mL) was added to the reactor. The content was cooled to 0° C. and purged with nitrogen three times. The reactor was then purged with hydrogen and pressurized to 90 psig. The reaction was aged with agitation at 0° C. for 7.5 h and conversion was monitored by the hydrogen uptake. The content was then warmed to RT and hydrogen was vented. After purging with nitrogen, the contents were drained. The reaction mixture was heated to 50° C. and filtered through a pad of Celite. The solution was concentrated to ~50% volume (150 mL) and diluted with toluene (5.9 g, 5 wt %). The suspension was heated to 65° C. and water (14.7 mL) was added dropwise to form a cloudy solution. The slurry was slowly cooled to −10° C. and aged for 30 minutes. The solid was filtered and washed with cold IPA (2×45 mL). The cake was dried under vacuum at 45° C. overnight to afford 20.0 g (83% yield) of (1R,4S)-acetamide (5) (>99% de). $^1$H NMR (CDCl$_3$) 400 MHz δ 7.34 (dd, 2H, J=7.9, 2.4 Hz), 7.23 (t, 1H, J=7.5 Hz), 7.15 (m, 2H), 6.85 (dd, 1H, J=8.2, 2.0 Hz), 6.82 (d, 1H, J=7.7 Hz), 5.72 (d, 1H, J=8.4 Hz), 5.31 (dd, 1H, J=13.2, 8.1 Hz), 4.10 (dd, 1H, J=7.0, 5.9 Hz), 2.17 (m, 2H), 2.06 (s, 3H), 1.87 (m, 1H). 1.72 (m, 1H); $^{13}$C NMR (CDCl$_3$) 100 MHz δ 169.7, 146.9, 138.8, 137.7, 132.6, 130.8, 130.6, 130.5, 130.3, 128.4, 128.3, 127.9, 127.4, 47.9, 44.9, 30.5, 28.4, 23.8.

Synthesis of amine hydrochloride (6) ((1R,4S)-4-(3,4-dichlorophenyl)-1,2,3,4-tetrahydronaphthalen-1-amine hydrochloride)

A solution of (1R,4S)-acetamide (5) (9.0 g, 26.9 mmol), n-propanol (45 mL) and 5M hydrochloric acid (45 mL) was refluxed for approximately 48 h (90-93° C.). During this time, the reaction temperature was maintained at ≥90° C. by periodically collecting the distillate until the reaction temperature was ≥92° C. Additional n-propanol was added periodically to maintain the solution at its original volume. After the hydrolysis was complete, the solution was slowly cooled to 0° C., resulting in a slurry, which was aged for one hour at 0° C. The reaction mixture was filtered, and the cake was washed with 1:1 methanol/water (20 mL), followed by t-butyl methyl ether (20 mL). The wet-cake was dried under vacuum at 45 to 50° C. to afford 7.0 g of the amine hydrochloride (6) (80% yield). $^1$H NMR (DMSO-d$_6$) δ 1.81-1.93 (m, 2H), 2.12-2.21 (m, 1H), 2.28-2.36 (m, 1H), 4.28 (t, 1H, J=6.8), 4.59 (br.s, 1H), 6.84 (d, 1H, J=7.6), 7.05 (dd, 1H, J=8.4, 1.6), 7.25 (t, 1H, J=7.6), 7.32 (t, 1H, J=7.6), 7.37 (d, 1H, J=1.6), 7.56 (d, 1H, J=8.4), 7.76 (d, 1H, J=7.2), 8.80 (br.s, 3H); $^{13}$C NMR (DMSO-d$_6$) 147.4, 138.9, 133.6, 131.0, 130.5, 130.4, 130.1, 129.0, 128.9, 128.4, 128.2, 126.8, 47.9, 43.1, 27.8, 25.2.

Synthesis of amine hydrochloride (6) via Asymmetric Hydrogenation Catalyzed by (R,R)-Norphos(COD)Rh—BF$_4$ A slurry of enamide (4) (60.4 g, 0.18 mol), in isopropanol (595.0 g) was purged of oxygen with vacuum/nitrogen cycles. The homogeneous catalyst precursor (referred to as a "catalyst"), (R,R)-Norphos(COD)Rh—BF$_4$ was added as a solution in methanol (34.6 mg, 0.025 mol %, 0.53 mL). After purging the system with hydrogen several times, the vessel was filled with hydrogen at the desired reaction pressure (approx 7 bar). The mixture was stirred at 25° C. and reaction progress was monitored by hydrogen uptake. Once the reaction was judged to be complete (hydrogen uptake and HPLC), the pressure was released and the system was purged repeatedly with nitrogen. The light yellow slurry was diluted with isopropanol (194.7 g), heated to dissolution (65° C.) and polish filtered. The mixture was heated to reflux to dissolve all solids. The solution was slowly cooled to 60-65° C. at which time the product crystallized. The antisolvent, water (262 g), was added at about 60-65° C., then the mixture was cooled to 0° C. over two hours and held at that temperature for aging. Filtration of the lightly colored solid was followed by washing with cold isopropanol (2×61 g). Drying of the off white solid under reduced pressure at 50-55° C. provided the (1R,4S)-acetamide (5) in 99% de (56.6 g, 93% yield).

A solution of (1R,4S)-acetamide (5) in dry THF (212.7 g, 239.3 mL) was treated with dry pyridine (8.7 g, 8.9 mL, 110 mmol). The resulting clear, colorless solution was cooled to approximately 0° C. Oxalyl chloride (12.9 g, 8.9 mL, 101.6 mmol) was added dropwise to the stirred solution, with care to control the exotherm and effervescence of CO and $CO_2$. The addition of the activating reagent was accompanied by the formation of a slurry. The slurry was allowed to stir cold for a short period (approx. 15 min) prior to sampling for conversion assessment. Once the reaction was complete, dry propylene glycol was added to the reaction, resulting in a minor exotherm. The reaction was warmed to 25° C., during which time the slurry changed in color and consistency. HPLC analysis of a second sample showed completion before the addition of 1-propanol (96.9 g, 120.5 mL). 6N HCl (128.0 g, 120.0 mL) was added. The mixture was heated to effect dissolution and the resulting mixture was polish filtered. THF was removed by atmospheric distillation. After concentration of the mixture, it was slowly cooled to 3° C. The resulting lightly colored slurry was filtered to yield and off-white cake. The cake was first washed with 17 wt % n-PrOH in deionized water (72.6 g, 75 mL total) and then with cold MtBE (55.5 g, 75 mL). The off-white wet cake was dried under vacuum at 45-50° C. The amine hydrochloride (6) was recovered as an off-white to white solid (24.8 g, 84.1% yield) with excellent purity (>99% purity by HPLC). Alternatively, the cake may be washed with methanol in water followed by methanol in methyl tert-butyl ether, and recrystallized from methanol/methyl tert-butyl ether.

Large Batch Synthesis of Enamide (4)

A larger-scaled synthesis of enamide (4) was completed using a process similar to the ones described herein. In this larger-scaled synthesis, ketone (1) (100 kg) was charged to a reactor with hydroxylamine hydrochloride (28.7 kg) and sodium acetate (33.8 kg) followed by toluene (350 kg) and methanol (14 kg). The mixture was heated to approximately 80° C. and allowed to react until the ketone (1) starting material was not more than 1.5% by HPLC. The completed reaction mixture was extracted with DI water at approximately 25° C. The aqueous phase was separated and the organic phase was washed with DI water to afford oxime (2). Iron(II) chloride in DI water was added followed by toluene. The volume of this solution was reduced by distillation.

Acetic anhydride (38.5 kg) was added to afford O-acetyloxime intermediate (3). Triethylphosphine (44.6 kg) was charged and the reaction mixture was slowly heated and allowed to react slightly under reflux until the remaining O-acetyloxime intermediate (3) was not more than 2.0% by HPLC.

The reaction mixture, comprising enamide (4) and diacylated enamine (4A) was cooled to about 20-25° C. and 6N NaOH was added. Tetrabutylammonium hydroxide was added and the enamide (4) by-product was hydrolyzed at about 25-30° C. The biphasic mixture was then allowed to phase separate and the aqueous phase was discarded. Subsequently, the organic phase was washed with 1% acetic acid aqueous solution until the pH was NMT 7.0. The aqueous phase was removed and the organic phase was washed with water. Toluene was added, the organic phase was concentrated and the warm solution was polish filtered. The solution was cooled to initiate crystallization. n-Heptane was added, the slurry was aged and cooled to about 20° C. The intermediate was filtered and washed twice with a solution consisting of a mixture of n-heptane and toluene. The intermediate was vacuum dried at not more than about 45° C. to yield enamide (4) (85% yield).

B. Synthesis of N-(1-cyclohexylideneethyl)acetamide

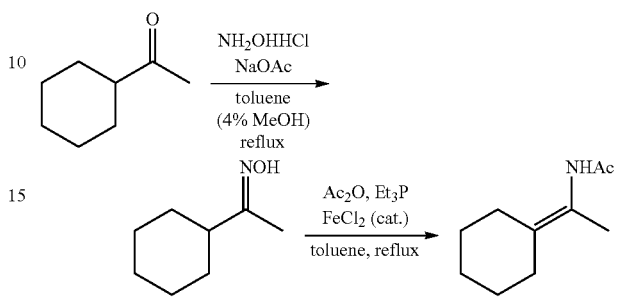

A mixture of hydroxylamine hydrochloride (6.6 g, 95.0 mmol), sodium acetate (7.8 g, 95.1 mmol), toluene (40 mL), methanol (1.4 mL) and cyclohexyl methyl ketone (10 g, 79.2 mmol) was heated to reflux (~90° C.). After about 1 h, the reaction was cooled to about room temperature and extracted with water (2×20 mL). The toluene solvent was removed by rotary evaporation and high vacuum to provide 10.1 grams (91% yield) of oxime: m.p. 63-64° C. $^1$H and $^{13}$C NMR spectra were consistent to published data (Moran, J.; Gorelsky, S. I.; Dimitrijevic, E; Lebrun, M.; Bedard, A.; Seguin, C.; Beauchemin, A., M.; J. Am. Chem. Soc., 130, 2008, 17893). The crude oxime was used directly in the next reaction without further purification.

To a solution of 1-cyclohexylethanone oxime (5.0 g, 35.4 mmol) and toluene (30 mL) at 20° C. was added dropwise acetic anhydride (4.0 g, 39.2 mmol). The solution was cooled to about room temperature over about 20 minutes and 32 mg of $FeCl_2.4H_2O$ (1792 ppm iron) and triethylphosphine (4.6 g, 38.9 mmol) were added. The reaction mixture was slowly heated and stirred overnight at reflux (~115° C.). Next, the reaction mixture was cooled to about room temperature and 1 wt % aq. $CuSO_4$ (50 mL) and EtOAc (100 mL) were added. The two liquid layers were separated. The organic phase was washed with sat. aq. NaCl (25 mL) and dried over $Na_2SO_4$. The organic phase was filtered and the solvent removed by rotary evaporation and high vacuum to provide 6.7 g of a crude solid. The material was triturated with hexanes (15 mL), filtered and washed with hexanes (5 mL) to afford 2.4 g (41% yield) of product: m.p. 85-86° C. (dec); TLC: $R_f$=0.19 (hexanes:EtOAc, 3:2, phosphomolybdic acid stain and heat).

$^1$H NMR (400 MHz, $CDCl_3$, 4:1 mixture of rotamers) 6=6.71 (bs, 0.8H), 6.46 (bs, 0.2H), 2.20-2.12 (m, 2.7H), 2.07-2.04 (m, 1.6H), 1.99 (s, 2.2H), 1.88 (s, 0.6H), 1.83 (s, 2.2H), 1.80 (s, 0.6H), 1.41-1.53 (m, 6H) ppm. $^{13}$C NMR (100 MHz, $CDCl_3$, 4:1 mixture of rotamers) 6=173.1 (minor), 169.0 (major), 137.6 (minor), 133.3 (major), 121.8 (minor), 121.1 (major), 30.2 (minor), 29.8 (major), 29.50 (minor), 29.47 (major), 27.44 (major), 27.35 (major), 27.2 (minor), 26.5 (major), 26.4 (minor), 23.4 (major), 19.7 (minor), 18.9 (minor), 17.0 (major) ppm; HRMS: calcd. for $C_{10}H_{17}NO$ [M+H]$^+$: 168.1383, found 168.1376.

C. Synthesis of N-(non-4-en-5-yl)acetamide

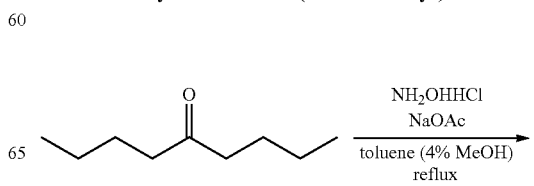

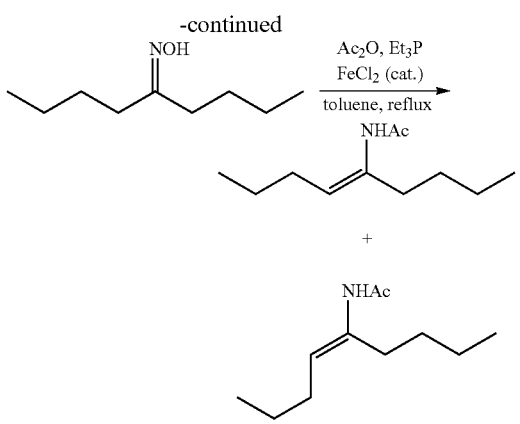

A mixture of hydroxylamine hydrochloride (5.9 g, 84.9 mmol), sodium acetate (6.9 g, 84.4 mmol), toluene (40 mL), methanol (1.4 mL) and 5-nonanone (10 g, 70.3 mmol) was heated to reflux (~88° C.). After about 1.5 h, the reaction was cooled to about room temperature and extracted with water (2×20 mL). The toluene solvent was removed by rotary evaporation and high vacuum to provide 11.0 grams (100% yield) of oxime as a liquid. $^1$H and $^{13}$C NMR spectra were consistent with published data (Moran, J.; Pfeiffer, J. Y.; Gorelsky, S., I.; Beauchemin, A., M.; Org. Lett., 11, 2009, 1895). The crude oxime was used directly in the next reaction without further purification.

To a solution of 5-nonanone oxime (5.0 g, 31.7 mmol) and toluene (30 mL) at about 21° C. was added dropwise acetic anhydride (3.6 g, 35.0 mmol). The solution was cooled from about 34° C. to about room temperature over about 25 minutes and 29 mg of FeCl$_2$.4H$_2$O (1624 ppm iron) and triethylphosphine (4.1 g, 35.0 mmol) were added. The solution was slowly heated and stirred overnight at reflux (~115° C.). Next, the solution was cooled to about room temperature and 1 wt % aq. CuSO$_4$ (50 mL) and EtOAc (100 mL) were added. The two liquid layers were separated. The organic phase was washed with sat. aq. NaCl (25 mL) and dried over Na$_2$SO$_4$. The organic phase was filtered and the solvent removed by rotary evaporation to afford a liquid. The crude material was purified by flash column chromatography on silica gel (hexanes:EtOAc, 4:1 to 7:3 gradient) to afford 3.6 g (62% yield) of product; TLC: R$_f$=0.15 (hexanes:EtOAc, 8:2, phosphomolybdic acid stain and heat). By NMR the product appeared to be about a 1:1.5 mixture of Z and E isomers. $^1$H NMR (400 MHz, CDCl$_3$) δ=7.27/7.18 (bs, 1H), 5.63/4.96 (t, J=7.3 Hz, 1H), 2.19-2.11 (m, 2H), 1.95/1.91 (s, 3H), 1.95-1.82 (m, 2H), 1.34-1.17 (m, 6H), 0.83-0.77 (m, 6H) ppm. $^{13}$C NMR (100 MHz, CDCl$_3$) δ=169.1, 168.7, 134.8, 134.6, 121.9, 118.3, 34.7, 30.2, 29.7, 29.4, 29.2, 24.1, 23.4, 23.2, 22.42, 22.39, 22.2, 13.95, 13.91, 13.84 ppm; HRMS: calcd. for C$_{11}$H$_{21}$NO [M+H]$^+$: 184.1696; found 184.1689. The E and Z geometric isomers may be separated by routine processes well known to those of skill in the art and then carried separately to chiral amides and amines.

The three examples, one with a linear dialkyl ketone, one with a cyclic alkyl ketone and one with an arylalkyl ketone demonstrate the generality of the reaction for ketones and their oximes in which there is at least one proton on an sp3 carbon adjacent the ketone.

D. Iron PPM Acceleration

To confirm that ppm levels of iron accelerate the reaction, four well-controlled laboratory experiments studied the effect of dosing a small amount of iron at the beginning of the enacetamide reaction. The results are shown in FIG. 1.

Adding 25, 38 and 50 ppm of iron (as FeCl$_2$) to the reaction along with acetic anhydride and triethyl phosphine after completion of the (S)-oxime aqueous work-up resulted in complete reaction in less than two hours. A control experiment was performed using ketone (1) that had been assayed by ICP-MS and contained less than 0.2 ppm Fe. The control had not yet reached completion at 19 hours.

To ascertain whether iron might have fortuitously affected reaction rates in earlier disclosed conversions of oximes to enamides, different batches of tetralone from the supplier for the experiments in PCT WO 2007/115185 were assayed by ICP-MS and found to contain from 1.99 ppm to 9.78 ppm iron. Reactions with these batches of tetralone were generally complete in about 6-16 hours; the speed of reaction varied roughly as a function of the amount of iron contaminant. One may surmise that the correlation between iron levels and reaction speed in samples with low levels of iron was not uniform because, at levels below 10 ppm, one has not reached a threshold for reproducible catalysis.

Figure 2:
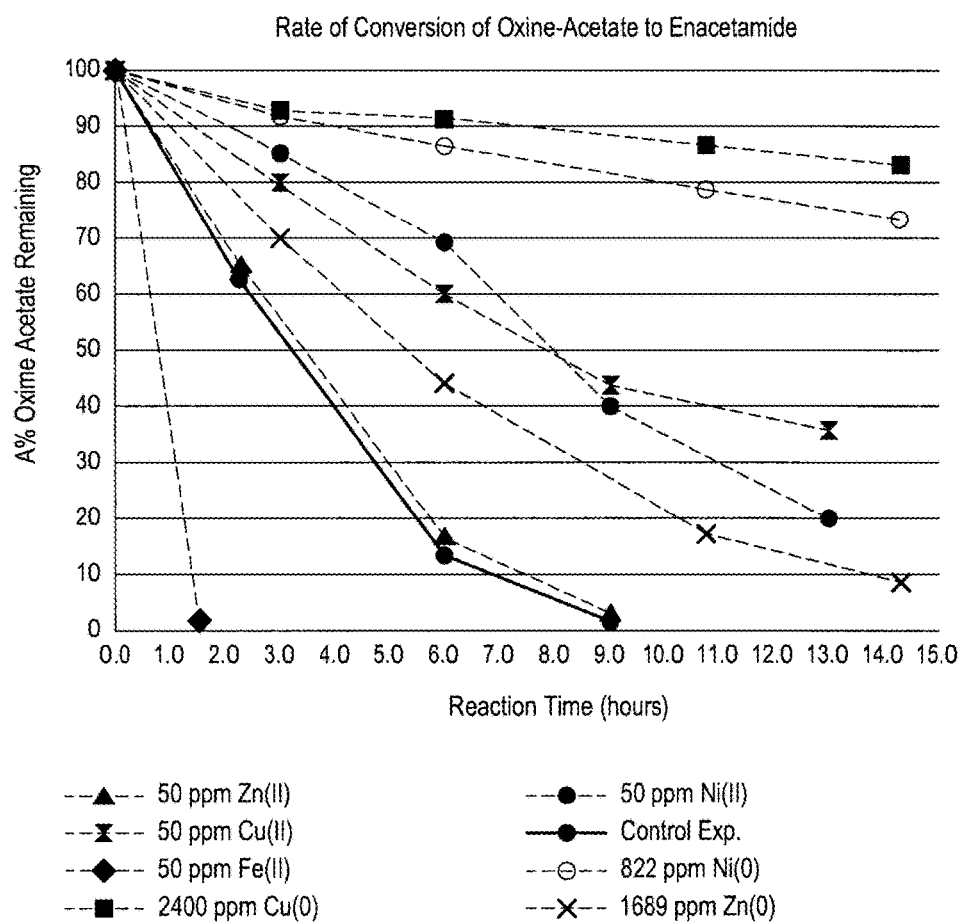
FIG. 2 is a graph of reaction speed reflected as percent residual oxime acetate versus time in hours in the presence of iron, zinc, nickel, and copper.

Inasmuch as other metals are disclosed in the literature as reducing agents for acetyloximes, zinc, copper and nickel were examined as possible catalysts with triethyl phosphine. The results are shown in FIG. 2. Zn(OAc)$_2$, had no catalytic effect; Zn(0), NiCl$_2$, CuOAc$_2$, Ni(0) and Cu(0)) retarded the reaction. The catalytic effect appears to be limited to iron.

Figure 3:
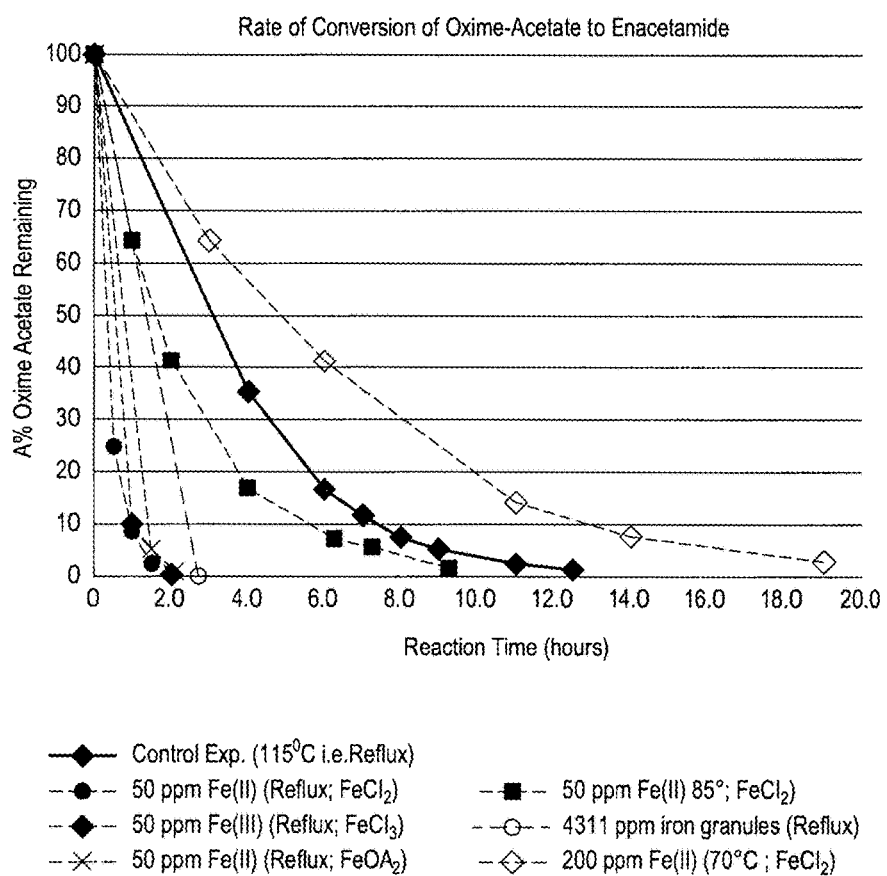
FIG. 3 is a graph of reaction speed reflected as percent residual oxime acetate versus time in hours in the presence of iron under various temperature regimes

The effect of temperature on the reaction was also examined. FIG. 3 shows the results. Using 50 ppm iron (as chloride or acetate salts) and 4311 ppm elemental iron as granules, it can be seen that, at 70° C. the reaction with tetralone acetyloxime is slower than the uncatalyzed reaction at 115° C., whereas at 85° C. the reaction is faster than uncatalyzed at 115° C., and at 115° C. the reaction is complete in about ⅙ the time. While iron at 70° C. was slower than uncatalyzed at 115° C., it still went to completion at 70° C., which suggests that, if one had a substrate that was unstable at higher temperatures, the iron-catalyzed reaction would be superior because it could be run at lower temperatures and produce better yields of cleaner products in less time than the corresponding uncatalyzed reaction.

What is claimed:

1. A process for converting an oxime to an enamide, said process comprising contacting said oxime with an acyl donor and a phosphine in the presence of an iron reagent that provides from 10 to 2000 ppm iron based on weight of iron in the iron reagent to weight of the corresponding ketone of the oxime under conditions that convert said oxime to said enamide.

2. The process according to claim 1 wherein the acyl donor is acetic anhydride.

3. The process according to claim 1 wherein the phosphine is chosen from tri n-butylphosphine, triethyl phosphine, 1,2-bisdiphenylphosphinoethane and triphenyl phosphine.

4. The process according to claim 3 wherein the phosphine is triethyl phosphine.

5. The process according to claim 1 wherein the iron reagent is chosen from elemental iron and Fe(II) salts and Fe(III) salts wherein the counter ion is halide or alkanoate.

6. The process according to claim 5 wherein the iron reagent is chosen from FeCl$_2$ and Fe(OAc)$_2$.

7. The process according to claim 1 wherein said iron reagent provides from 10 to 100 ppm iron.

8. The process according to claim 1 wherein said iron reagent provides from 10 to 50 ppm iron.

9. The process according to claim 1 wherein said iron reagent provides from 25 to 100 ppm iron.

10. The process according to claim 1 wherein said iron reagent provides from 500 to 2000 ppm iron.

11. The process according to claim 1 wherein said process is carried out in a solvent at a temperature between 80° C. and 150° C.

12. The process of claim 11 wherein said solvent is toluene.

13. The process according to claim 1 wherein the oxime is an oxime of an aliphatic ketone.

14. The process according to claim 1 wherein the oxime is a tetralone an oxime of a tetralone.

15. A process for converting a ketone to an enamide, said process comprising the sequential steps of:
(a) reacting said ketone with hydroxylamine to provide an oxime; and
(b) reacting said oxime with an acyl donor and a phosphine in the presence of an iron reagent that provides from 10 to 2000 ppm iron based on weight of iron in the iron reagent to weight of the ketone.

16. A process for converting a prochiral ketone to an enantiomerically enriched chiral amide, said process comprising:
(a) reacting said ketone with hydroxylamine to provide an oxime;
(b) reacting said oxime with an acyl donor and a phosphine in the presence of an iron reagent that provides from 10 to 2000 ppm iron based on weight of iron in the iron reagent to weight of the ketone to provide an enamide; and
(c) reducing said enamide with hydrogen in the presence of a chiral catalyst to produce an enantiomerically enriched chiral amide.

17. A process for converting a prochiral ketone to an enantiomerically enriched chiral amine, said process comprising:
(a) reacting said ketone with hydroxylamine to provide an oxime;
(b) reacting said oxime with an acyl donor and a phosphine in the presence of an iron reagent that provides from 10 to 2000 ppm iron based on weight of iron in the iron reagent to weight of the ketone to provide an enamide;
(c) reducing said enamide with hydrogen in the presence of a chiral catalyst to produce an enantiomerically enriched chiral amide; and
(d) hydrolyzing said chiral amide to an enantiomerically enriched chiral amine.

18. The process of claim 15 wherein the acyl donor is acetic anhydride, the phosphine is triethyl phosphine and the iron reagent is chosen from $FeCl_2$ and $Fe(OAc)_2$.

19. The process of claim 16 wherein the acyl donor is acetic anhydride, the phosphine is triethyl phosphine and the iron reagent is chosen from $FeCl_2$ and $Fe(OAc)_2$.

20. The process of claim 17 wherein the acyl donor is acetic anhydride, the phosphine is triethyl phosphine and the iron reagent is chosen from $FeCl_2$ and $Fe(OAc)_2$.

21. The process of claim 15 wherein steps (a) and (b) are carried out without isolation of the oxime.

22. The process of claim 16 wherein steps (a) and (b) are carried out without isolation of the oxime.

23. The process of claim 17 wherein steps (a) and (b) are carried out without isolation of the oxime.

* * * * *

UNITED STATES PATENT AND TRADEMARK OFFICE
CERTIFICATE OF CORRECTION

PATENT NO. : 10,435,351 B2
APPLICATION NO. : 15/882498
DATED : October 8, 2019
INVENTOR(S) : Vandenbossche et al.

Page 1 of 1

It is certified that error appears in the above-identified patent and that said Letters Patent is hereby corrected as shown below:

In the Claims

Column 35, Line 6: Claim 14, Delete the first instance of "a tetralone"

Signed and Sealed this
Twenty-sixth Day of November, 2019

Andrei Iancu
*Director of the United States Patent and Trademark Office*